United States Patent [19]

Hui et al.

[11] Patent Number: 5,502,061
[45] Date of Patent: Mar. 26, 1996

[54] PEPTIDYL SUBSTITUTED BENZAMIDES AND NAPHTHAMIES

[75] Inventors: Kwan Y. Hui, Carmel; Charles D. Jones, Indianapolis; Louis N. Jungheim, Indianapolis; Pamela A. Pennington, Indianapolis, all of Ind.

[73] Assignee: Eli Lilly and Company, Indianapolis, Ind.

[21] Appl. No.: 312,491

[22] Filed: Sep. 26, 1994

Related U.S. Application Data

[63] Continuation of Ser. No. 995,282, Dec. 22, 1992, abandoned.

[51] Int. Cl.$^6$ .................. A61K 37/02; C07D 213/40; C07D 295/26; C07D 303/36; C07C 49/11; C07C 31/125; C07C 251/38; C07C 275/18

[52] U.S. Cl. .............. 514/311; 514/399; 514/415; 514/432; 514/436; 514/529; 514/532; 514/534; 514/539; 514/616; 514/617; 514/618; 514/619; 514/620; 546/176; 548/338.1; 548/457; 548/504; 548/506; 549/57; 560/24; 560/27; 560/28; 564/154; 564/155; 564/156; 564/157; 564/158

[58] Field of Search .................. 548/338.1, 457, 548/504, 505, 506; 564/155, 156, 157, 158, 154; 560/24, 27, 28; 514/311, 319, 415, 436, 529, 432, 532, 534, 539, 616, 617, 618, 619, 620; 546/176; 549/57

[56] References Cited

U.S. PATENT DOCUMENTS

| 4,657,931 | 4/1987 | Baran et al. | 514/616 |
| 4,760,180 | 7/1988 | Pitzele et al. | 564/157 |
| 4,822,775 | 4/1989 | Hansen et al. | 514/19 |
| 4,845,079 | 7/1989 | Luly et al. | 514/18 |
| 4,963,530 | 10/1990 | Hemmi et al. | 514/19 |
| 5,032,577 | 7/1991 | Fung et al. | 514/18 |
| 5,142,056 | 8/1992 | Kempe et al. | 546/265 |
| 5,147,888 | 9/1992 | Hanson et al. | 514/419 |
| 5,175,181 | 12/1992 | Hanson et al. | 514/400 |

FOREIGN PATENT DOCUMENTS

| 0006298 | 1/1980 | European Pat. Off. | 564/155 |
| 0172347 | 2/1986 | European Pat. Off. | 548/338.5 |
| 0217286 | 4/1987 | European Pat. Off. | 564/157 |
| 0317959 | 5/1989 | European Pat. Off. | 564/157 |
| 0337714 | 10/1989 | European Pat. Off. | 546/265 |
| 0346847 | 12/1989 | European Pat. Off. | 546/265 |
| 0361341 | 4/1990 | European Pat. Off. | 546/265 |
| 0402646 | 12/1990 | European Pat. Off. | 546/365 |

OTHER PUBLICATIONS

Roberts, N. A. et al., *Science*, 248, 358–361 (1990).

Vara Prasad, J. V. N. et al., Peptides, Chemistry and Biology, Proceedings of the Twelfth American Peptide Symposium, Jun. 16–21, 721–722 (1991).

Thaisrivongs, S. et al., *J. Med Chem*, 34, 2344–2356 (1991).

*Primary Examiner*—Floyd D. Higel
*Attorney, Agent, or Firm*—Janet T. McClain

[57] ABSTRACT

The present invention provides HIV protease inhibitors, pharmaceutical formulations containing those compounds and methods of treating and/or preventing HIV infection and/or AIDS.

32 Claims, No Drawings

PEPTIDYL SUBSTITUTED BENZAMIDES AND NAPHTHAMIES

This application is a continuation-in-part continuation of application Ser. No. 07/995,282, filed on Dec. 22, 1992, now abandoned.

BACKGROUND OF THE INVENTION

A retrovirus designated human immuno-deficiency virus (HIV) is the causative agent of the complex disease termed Acquired Immune Deficiency Syndrome (AIDS), and is a member of the lentivirus family of retroviruses. M. A. Gonda, F. Wong-Staal, R. C. Gallo, "Sequence Homology and Morphological Similarity of HTLV III And Visna Virus, A Pathogenic Lentivirus", Science, 227, 173, (1985); P. Sonigo, N. Alizon, et al., "Nucleotide Sequence of the Visna Lentivirus: Relationship to the AIDS Virus", Cell, 42, 369, (1985). The complex disease AIDS includes progressive destruction of the immune system and degeneration of the central and peripheral nervous systems. The HIV virus was previously known or referred to as LAV, HTLV-III or ARV.

A common feature of retrovirus replication is the post-translational processing of precursor polyproteins by a virally encoded protease to generate mature viral proteins required for vital assembly and function. Interruption of this processing appears to prevent the production of normally infectious virus. Unprocessed structural proteins also have been observed in clones of non-infectious HIV strains isolated from human patients. The results suggest that the inhibition of HIV protease represents a viable method for the treatment of AIDS and the prevention or treatment of infection by HIV.

The HIV genome encodes structural protein precursors known as gag and pot, which are processed to afford the protease, reverse transcriptase and endonuclease/integrase. The protease further cleaves gag and gag-pol polyproteins to yield mature structural proteins of the virus core.

Considerable efforts are being directed toward the control of HIV by means of the structural protein precursors which are processed to yield the retroviral protease, reverse transcripcase and endonuclease/integrase. For example, the currently used therapeutic, AZT, is an inhibitor of the viral reverse transcriptase. H. Mitsuya, NS. Broder, "Inhibition of the In Vitro Infectivity in Cytopathic Effects of HTLV III", Proc. Natl. Acad. Sci. USA, 83, 1911 (1986).

Research efforts have also been directed toward HIV protease inhibitors. For example, European Patent Application (EPA) 361 341; EPA 346 847; EPA 402 646; and EPA 337 714 all disclose compounds which are said to be useful as HIV protease inhibitors.

Unfortunately, many of the known compounds suffer from toxicity problems, lack of bioavailability or short in vivo half-lives. Thus, despite the recognized therapeutic potential associated with a protease inhibitor and the research efforts expended thus far, a viable therapeutic agent has not yet emerged.

Accordingly, a primary object of the present invention is to provide novel HIV protease inhibitors which are useful in the treatment or prevention of HIV infection and/or the resulting acquired immune deficiency syndrome (AIDS).

A further object of the present invention is to provide therapeutic compositions that are useful in the treatment or prevention of both HIV infection and AIDS.

Still another object is to provide methods for the treatment or prevention of HIV infection and/or the AIDS.

Other objects, features and advantages will become apparent to those skilled in the art from the following description and claims.

SUMMARY OF THE INVENTION

The present invention relates to compounds of formula I, below, and pharmaceutically acceptable salts thereof that inhibit the protease encoded by human immunodeficiency virus (HIV) type 1 (HIV-1) or type 2 (HIV-2). These compounds are useful in the treatment or prevention of HIV infection and the treatment or prevention of the resulting acquired immune deficiency syndrome (AIDS). The compounds, their pharmaceutically acceptable salts, and the pharmaceutical compositions can be used alone or in combination with other antivirals, immunomodulators, antibiotics or vaccines. Methods of treating or preventing AIDS, methods of treating or preventing HIV infection and methods of inhibiting HIV replication are disclosed.

The present invention relates to a method of inhibiting HIV replication in an HIV infected cell, a cell susceptible to HIV infection or a primate in need thereof, thus treating or preventing HIV infection and/or AIDS, comprising administering an effective amount of a compound of formula I

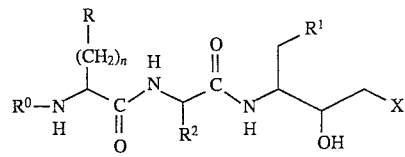

wherein:

$R^0$ is hydrogen, $C_1$–$C_6$ alkoxycarbonyl or $C_2$–$C_6$ alkanoyl;

n is 0, 1 or 2;

R is aryl, heterocycle or unsaturated heterocycle;

$R^1$ is aryl, $C_5$–$C_7$ cycloalkyl or —S—$R^{1x}$, where $R^{1x}$ is aryl or $C_5$–$C_7$ cycloalkyl;

$R^2$ is an amino acid side chain, cyano($C_1$–$C_4$)alkyl, —$CH_2SCH_3$ or —$CH_2C(O)$—$R^{2a}$, where $R^{2a}$ is $C_1$–$C_4$ alkylamino;

X is a group having the structure:

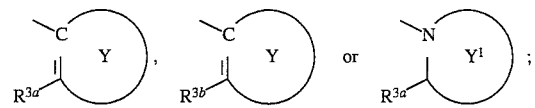

Y is aryl or unsaturated heterocycle;
y1 is heterocycle;
$R^{3a}$ is a group having the structure:
1) —C(O)—$NR^4R^4$,

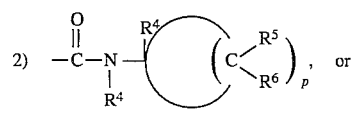

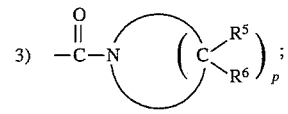

$R^{3b}$ is a group having the structure:

1) $-\underset{R^5}{N}-\overset{O}{\underset{\|}{C}}-R^6,$

2) $-\underset{R^4}{N}-\overset{O}{\underset{\|}{C}}-NR^4R^4,$ or

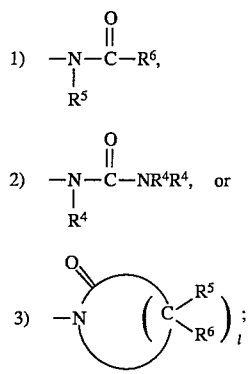

p is 4 or 5;
l is 3, 4 or 5;
$R^4$ at each occurrence is independently hydrogen, $C_1-C_6$ alkyl or hydroxy($C_1-C_4$)alkyl;
$R^5$ and $R^6$ are independently selected from hydrogen, hydroxy, $C_1-C_6$ alkyl, $C_1-C_6$ alkoxy, amino, $C_1-C_4$ alkylamino, hydroxy($C_1-C_4$)alkyl, carboxy, $C_1-C_4$ alkoxycarbonyl, carbamoyl, N-($C_1-C_4$)alkylcarbamoyl, aryl, heterocycle or unsaturated heterocycle; or a pharmaceutically acceptable salt thereof.

The present invention also relates to a compound of formula I, or a pharmaceutically acceptable salt thereof, wherein R, $R^0$, $R^1$, $R^2$, X and n are as defined above in formula I.

The present invention further provides pharmaceutical formulations comprising a compound of formula I or a pharmaceutically acceptable salt thereof, in combination with a pharmaceutically acceptable carrier, diluent or excipient therefor.

DETAILED DESCRIPTION OF THE INVENTION

The present invention provides new compounds of formula I, as described above, that are useful for treating or preventing HIV infection and/or AIDS.

All temperatures stated herein are in degrees Celsius (° C.). All units of measurement employed herein are in weight units except for liquids which are in volume units.

As used herein, the term "$C_1-C_6$ alkyl" represents a straight or branched alkyl chain having from one to six carbon atoms. Typical $C_1-C_6$ alkyl groups include methyl, ethyl, propyl, isopropyl, butyl, isobutyl, sec-butyl, t-butyl, pentyl, neo-pentyl, hexyl and the like. The term "$C_1-C_6$ alkyl" includes within its definition the term "$C_1-C_4$ alkyl".

"Halo" represents chloro, fluoro, bromo or iodo.

"Halo($C_1-C_4$)alkyl" represents a straight or branched alkyl chain having from one to four carbon atoms with 1–3 halogen atoms attached to it. Typical halo($C_1-C_4$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl and the like.

"Hydroxy($C_1-C_4$)alkyl" represents a straight or branched alkyl chain having from one to four carbon atoms with an hydroxy group attached to it. Typical hydroxy($C_1-C_4$)alkyl groups include hydroxymethyl, 2-hydroxyethyl, 3-hydroxypropyl, 3-hydroxypropyl, 2-hydroxyisopropyl, 4-hydroxybutyl and the like.

"Cyano($C_1-C_4$)alkyl" represents a straight or branched alkyl chain having from one to four carbon atoms with an cyano group attached to it. Typical cyano($C_1-C_4$)alkyl groups include cyanomethyl, 2-cyanoethyl, 3-cyanopropyl, 3-cyanopropyl, 2-cyanoisopropyl, 4-cyanobutyl and the like.

"$C_1-C_6$ alkylthio" represents a straight or branched alkyl chain having from one to four carbon atoms attached to a sulfur atom. Typical $C_1-C_6$ alkylthio groups include methylthio, ethylthio, propylthio, isopropylthio, butylthio, sec-butylthio, t-butylthio, pentylthio, hexylthio and the like.

"$C_1-C_4$ alkylamino" represents a straight or branched alkyl chain having from one to four carbon atoms attached to an amino group. Typical $C_1-C_4$ alkylamino groups include methylamino, ethylamino, propylamino, isopropylamino, butylamino, sec-butylamino and the like.

"Di($C_1-C_4$)alkylamino" represents two straight or branched alkyl chains having from one to four carbon atoms attached to a common amino group. Typical di($C_1-C_4$)alkylamino groups include dimethylamino, ethylmethylamino, methylpropylamino, ethylisopropylamino, butylmethylamino, sec-butylethylamino and the like.

"$C_1-C_6$ alkoxy" represents a straight or branched alkyl chain having from one to six carbon atoms attached to an oxygen atom. Typical $C_1-C_6$ alkoxy groups include methoxy, ethoxy, propoxy, isopropoxy, butoxy, sec-butoxy, t-butoxy, pentoxy, hexoxy and the like. The term "$C_1-C_6$ alkoxy" includes within its definition the term "$C_1-C_4$ alkoxy".

"$C_2-C_6$ alkanoyl" represents a straight or branched alkyl chain having from one to six carbon atoms attached to a carbonyl moiety. Typical $C_2-C_6$ alkanoyl groups include ethanoyl, propanoyl, butanoyl, t-butanoyl, pentanoyl, 3-methylpentanoyl and the like.

"$C_1-C_6$ alkoxycarbonyl" represents a straight or branched alkoxy chain having from one to four carbon atoms attached to a carbonyl moiety. Typical $C_1-C_6$ alkoxycarbonyl groups include methoxycarbonyl, ethoxycarbonyl, propoxycarbonyl, isopropoxycarbonyl, butoxycarbonyl, t-butoxycarbonyl and the like. The term "$C_1-C_6$ alkoxycarbonyl" includes within its definition the term "$C_1-C_4$ alkoxycarbonyl".

"N-($C_1-C_4$)alkylcarbamoyl" represents a straight or branched alkyl chain having from one to four carbon atoms attached to the nitrogen atom of a carbamoyl moiety. Typical N-($C_1-C_4$)alkylcarbamoyl groups include N-methylcarbamoyl, N-ethylcarbamoyl, N-propylcarbamoyl, N-isopropylcarbamoyl, N-butylcarbamoyl and N-t-butylcarbamoyl and the like.

"Carbamoyl($C_1-C_4$)alkyl" represents a straight or branched alkyl chain having from one to four carbon atoms with a carbamoyl moiety attached to it. Typical carbamoyl($C_1-C_4$)alkyl groups include carbamoylmethyl, 2-carbamoylethyl, 3-carbamoylpropyl, 2-carbamoylisopropyl, 4-carbamoylbutyl and the like.

"$C_5-C_7$ cycloalkyl" represents a saturated hydrocarbon ring structure containing from five to seven carbon atoms which is unsubstituted or substituted with 1, 2 or 3 substituents independently selected from halo, halo($C_1-C_4$)alkyl, $C_1-C_4$ alkyl, $C_1-C_4$ alkoxy, carboxy, $C_1-C_4$ alkoxycarbonyl, carbamoyl, N-($C_1-C_4$)alkylcarbamoyl, amino, $C_1-C_4$ alkylamino, di($C_1-C_4$)alkylamino or a group having the structure $-(CH_2)_a-R^7$ where a is 1, 2, 3 or 4 and $R^7$ is hydroxy, $C_1-C_4$ alkoxy, carboxy, $C_1-C_4$ alkoxycarbonyl, amino, carbamoyl, $C_1-C_4$ alkylamino or di($C_1-C_4$)alkylamino. Typical $C_5-C_7$ cycloalkyl groups include cyclopentyl, cyclohexyl, cycloheptyl, 3-methylcyclopentyl, 4-ethoxycyclohexyl, 5-carboxycycloheptyl, 6-chlorocyclohexyl and the like.

The term "heterocycle" represents an unsubstituted or substituted stable 5- to 7-membered monocyclic or 7- to 10-membered bicyclic heterocyclic ring which is saturated and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The heterocyclic ring may be attached at any heteroatom or carbon atom which affords a stable structure. The heterocycle is unsubstituted or substituted with 1, 2 or 3 substituents independently selected from halo, halo($C_1$–$C_4$)alkyl, $C_1$–$C_4$ alkyl, $C_1$–$C_4$ alkoxy, carboxy, $C_1$–$C_4$ )alkoxycarbonyl, carbamoyl, N-($C_1$–$C_4$)alkylcarbamoyl, amino, $C_1$–$C_4$ alkylamino, di($C_1$–$C_4$)alkylamino or a group having the structure —$(CH_2)_a$-$R^7$ where a is 1, 2, 3 or 4 and $R^7$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino.

The term "unsaturated heterocycle" represents an unsubstituted or substituted stable 5- to 7-membered monocyclic or 7- to 10-membered bicyclic heterocyclic ring which has one or more double bonds and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The unsaturated heterocyclic ring may be attached at any heteroatom or carbon atom which affords a stable structure. The unsaturated heterocycle is unsubstituted or substituted with 1, 2 or 3 substituents independently selected from halo, halo ($C_1$–$C_4$)alkyl, $C_1$–$C_4$ alkyl, $C_1$–$C_4$ alkoxy, carboxy, $C_1$–$C_4$ alkoxycarbonyl, carbamoyl, N-($C_1$–$C_4$)alkylcarbamoyl, amino, $C_1$–$C_4$ alkylamino, di($C_1$–$C_4$)alkylamino or a group having the structure —$(CH_2)_a$-$R^7$ where a is 1, 2, 3 or 4 and $R^7$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino.

Examples of such heterocycles and unsaturated heterocycles include piperidinyl, piperazinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinylsulfoxide, thiamorpholinylsulfone, oxadiazolyl, triazolyl, tetrahydroquinolinyl, tetrahydrisoquinolinyl, 3-methylimidazolyl, 3-methoxypyridyl, 4-chloroquinolinyl, 4-aminothiazolyl, 8-methylquinolinyl, 6-chloroquinoxalinyl, 3-ethylpyridyl, 6-methoxybenzimidazolyl, 4-hydroxyfuryl 4-methylisoquinolinyl, 6,8-dibromoquinolinyl, 4,8-dimethylnaphthyl, 2-methyl-1,2,3,4-tetrahydroisoquinolinyl, N-methylquinolin-2-yl, 2-t-butoxycarbonyl-1,2,3,4-isoquinolin-7-yl and the like.

"Aryl" represents a phenyl or naphthyl ring that is optionally substituted with 1, 2 or 3 substituents independently selected from halo, morpholino($C_1$–$C_4$)alkoxy, pyridyl($C_1$–$C_4$)alkoxy, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, N-($C_1$–$C_4$)alkylcarbamoyl, amino, $C_1$–$C_4$ alkylamino, di($C_1$–$C_4$)alkylamino or a group having the structure, —$(CH_2)_a$-$R^7$ where a is 1, 2, 3 or 4; and $R^7$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino. Typical aryl groups include 4-methylphenyl, 3-ethylnaphthyl, 2,5-dimethylphenyl, 8-chloronaphthyl, 3-aminonaphthyl, 4-carboxyphenyl and the like.

"Heterocycle($C_1$–$C_4$)alkyl" represents a straight or branched alkyl chain having from one to four carbon atoms with a heterocycle group attached to it. "Unsaturated heterocycle($C_1$–$C_4$)alkyl" represents a straight or branched alkyl chain having from one to four carbon atoms with an unsaturated heterocycle group attached to it. Typical heterocycle($C_1$–$C_4$)alkyl and unsaturated heterocycle($C_1$–$C_4$)alkyl groups include pyrrolylmethyl, quinolinylmethyl, 1-indolylethyl, 2-furylethyl, 3-thien-2-ylpropyl, 1-imidazolylisopropyl, 4-thiazolylbutyl and the like.

"Aryl($C_1$–$C_4$)alkyl" represents a straight or branched alkyl chain having from one to four carbon atoms with an aryl group attached to it. Typical aryl($C_1$–$C_4$)alkyl groups include phenylmethyl, 2-phenylethyl, 3-naphthylpropyl, 1-naphthylisopropyl, 4-phenylbutyl and the like.

The third group in the definition of $R^3$ includes unsubstituted or substituted piperidinyl, and unsubstituted and substituted pyrrolidinyl where the substituents are selected from those defined for $R^5$ and $R^6$ such that the third group is a sterically feasible stable structure.

The term "amino acid side chain" represents the distinctive atom or group bonded to an α-carbon atom also having bonded thereto a carboxyl group and an amino group. The side chains are selected from those found on the following amino acids:

| | |
|---|---|
| Alanine | Ala |
| Arginine | Arg |
| Asparagine | Asn |
| Aspartic acid | Asp |
| Cysteine | Cys |
| Glutamine | Gln |
| Glutamic acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

The term "amino-protecting group" as used in the specification refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl and the urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxy-carbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; benzoylmethylsulfonyl, 2-nitrophenylsulfenyl, diphenylphosphine oxide and like amino-protecting groups. The species of amino-protecting group employed is not critical so long as the derivatized amino group is stable to the condition of subsequent reaction(s) on other positions of the intermediate molecule and can be selectively removed at the appropriate point without disrupting the remainder of the molecule including any other amino-protecting group(s). Preferred amino-protecting groups are t-butoxycarbonyl (t-Boc) and benzyloxy carbonyl (CbZ). Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and sons, New York, N.Y., 1981, Chapter 7.

The term "carboxy-protecting group" as used in the specification refers to substituents of the carboxy group commonly employed to block or protect the carboxy functionality while reacting other functional groups on the compound. Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylene-dioxybenzyl, benzhydryl, 4,4'-dimethoxybenzhydryl, 2,2',4,4'-tetramethoxy-benzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, β-(dibutylmethylsilyl)ethyl, p-toluenesulfonylethyl, 4-nitrobenzylsulfonylethyl, allyl, cinnamyl, 1-(trimethylsilylmethyl)prop-1-en-3-yl and like moieties. A preferred carboxy-protecting group is benzhydryl. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

The compounds of the present invention may have four asymmetric centers denoted by an asterisk in the formula below.

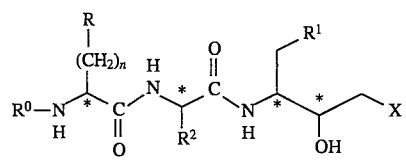

As a consequence of these asymmetric centers, the compounds of the present invention can occur as mixtures of diastereomers, racemic mixtures and as individual enantiomers. All asymmetric forms, individual isomers and combinations thereof, are within the scope of the present invention.

As mentioned above, the invention includes pharmaceutically acceptable salts of the compounds defined by formula I. Although generally neutral, a particular compound of this invention can possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosporic acid and the like, and, organic acids such as p-toluenesulfonic acid, methanesulfonic acid, oxalic acid, p-bromophenylsulfonic acid, carbonic acid, succinic acid, citric acid, benzoic acid, acetic acid and the like.

Examples of such pharmaceutically acceptable salts are sulfate, pyrosulfate, bisulfate, sulfite, bisulfite, phosphate, monohydrogenphosphate, dihydrogenphosphate, metaphosphate, pyrophosphate, chloride, bromide, iodide, acetate, proprionate, decanoate, caprylate, acrylate, formate, isobutyrate, caproate, heptanoate, propionate, oxalate, malonate, succinate, suberate, sebacate, fumarate, maleate, butyne-1, 4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylproprionate, phenylbutyrate, citrate, lactate, γ-hydroxybutyrate, glycollate, tartrate, methanesulfonate, propanesulfonate, naphthalene-1-sulfonate, naphthalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates and the like. Examples of such bases useful in preparing the salts of this invention include sodium hydroxide, potassium hydroxide, ammonium hydroxide, carbonate, potassium carbonate, bicarbonate, potassium bicarbonate, calcium hydroxide, calcium carbonate and the like. The potassium and sodium salt forms are particularly preferred.

It should be recognized that the particular counterion forming a part of any salt of this invention is not of a critical nature, as long as the salt as a whole is pharmacologically acceptable and as long as the counterion does not contribute undesired qualities to the salt as a whole.

Preferred compounds of this invention are those compounds of the formula

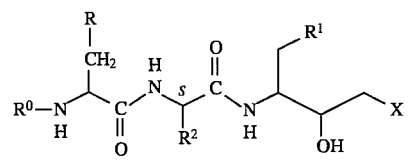

wherein:
R⁰ is hydrogen or $C_1$–$C_4$ alkoxycarbonyl;
R is aryl or unsaturated heterocycle;
$R^2$ is —CH(CH$_3$)$_2$, —CH$_2$—C(O)NH$_2$ or —CH$_2$—imidazol-4-yl;

$R^1$ is aryl or —S-$R^{1x}$ where $R^{1x}$ is aryl;
X is

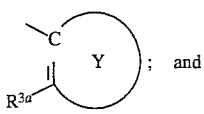
; and $R^{3a}$ is —C(O)NH(t-butyl); or a pharmaceutically acceptable salt thereof.

Of these preferred compounds, more preferred are those compounds wherein:
$R^0$ is t-butoxycarbonyl;
R is naphth-1-yl, phenyl or indol-3-yl;
$R^2$ is —$CH_2$—C(O)$NH_2$;
$R^1$ is phenyl; and
Y is phenyl;
or a pharmaceutically acceptable salt thereof.

The most preferred compounds are:
[2R-(2R*,3S*,6S*,9S*)]-N-t-butyl-2-[2-hydroxy-3-phenylmethyl-4,7-diaza-5,8-dioxo-6-(1-methylethyl)-9-N(t-butoxycarbonyl)amino-10-naphth-1-yl]decyl benzamide;

[2R-(2R*, 3S*, 6S*, 9R*)]-N-t-butyl-2-[2-hydroxy-3-phenylmethyl-4,7-diaza-5, 8-dioxo-6-(1-methylethyl)-9-N(t-butoxycarbonyl)amino-10-naphth-1-yl]decyl benzamide;

[2R- (2R*, 3S*, 6S*, 9R*)]-N- t-butyl-2-[2-hydroxy-3-phenylmethyl-4,7-diaza-5 8-dioxo-6-(carbamoylmethyl)-9-N(t-butoxycarbonyl)amino-10-naphth-1-yl]decyl benzamide;

[2R- (2R*, 3S*, 6S*, 9S*)]-N-t-butyl-2-[2-hydroxy-3-phenylmethyl-4,7-diaza-5, 8-dioxo-6-(carbamoylmethyl)-9-N(t-butoxycarbonyl)amino-10-phenyl]decyl benzamide;

[2R- (2R*, 3S*, 6S*, 9R*)]-N-t-butyl-2-[2-hydroxy-3-phenylmethyl-4,7-diaza-5, 8-dioxo-6-(imidazol-1-ylmethyl)-9-N(t-butoxycarbonyl)amino-10-naphth-1-yl]decyl benzamide;

[2R- (2R*, 3S*, 6S*, 9S*)]-N-t-butyl-2-[2-hydroxy-3-phenylmethyl-4,7-diaza-5, 8-dioxo-6-(carbamoylmethyl)-9-N(t-butoxycarbonyl)amino-10-indol-3-yl]decyl benzamide; and

[2R- (2R*, 3S*, 6S*, 9R*)]-N-t-butyl-2-[2-hydroxy-3-phenylmethyl-4,7-diaza-5, 8-dioxo-6-(carbamoylmethyl)-9-N(t-butoxycarbonyl)amino-10-indol-3-yl]decyl benzamide;
or a pharmaceutically acceptable salt thereof.

The following list of compounds is provided to further illustrate compounds of formula I included within the scope of the invention:

[2R-(2R*, 3S*, 6S*, 9S*)]-N-t-butyl-2-[2-hydroxy-3-phenylthiomethyl-4,7-diaza -5,8-dioxo-6-(carbamoylmethyl)-9-amino-10-naphth-1-yl]decyl benzamide;

[2R-(2R*, 3S*, 6S*, 9S*)]-N-t-butyl-2-[2-hydroxy-3-phenylthiomethyl-4,7-diaza -5,8-dioxo-6-(carbamoylmethyl)-9-amino-10-naphth-2-yl]decyl benzamide;

[2R- (2R*, 3S*, 6S*, 9S*)]-N-t-butyl-2-[2-hydroxy-3-naphthylthiomethyl-4,7-diaza -5,8-dioxo-6-(1-methylethyl)-9-amino-10-naphth-1-yl]decyl benzamide;

[2R- (2R*, 3S*, 6S*, 9S*)]-N-t-butyl-2-[2-hydroxy-3-phenylthiomethyl-4,7-diaza -5,8-dioxo-6-(carbamoylethyl)-9-amino-10-naphth-1-yl]decyl benzamide;

[2R-(2R*, 3S*, 6S*, 9R*)]-N-t-butyl-2-[2-hydroxy-3-phenylmethyl-4,7 -diaza -5,8-dioxo-6-(carboxymethyl)-9-amino-10-naphth-1-yl]decyl benzamide;

[2R- (2R*, 3S*, 6S*, 9S*)]-N-t-butyl-2-[2-hydroxy-3-phenylmethyl-4,7-diaza -5,8-dioxo-6-(methyl)-9-amino-10-naphth-1-yl]decyl benzamide;

[2R- (2R*, 3S*, 6S*, 9S*)]-N-t-butyl-2-[2-hydroxy-3-phenylmethyl-4,7 -diaza -5,8-dioxo-6-(carbamoylethyl)-9-amino-10-naphth-1-yl]decyl benzamide;

[2R- (2R*, 3S*, 6S*, 9R*)]-N-t-butyl-2-[2-hydroxy-3-phenylmethyl-4,7-diaza -5,8-dioxo-6-(carbamoylmethyl)-9-amino-10-quinolin-2-yl]decyl benzamide;

[2R- (2R*, 3S*, 6S*, 9S*)]-N-t-butyl-2-[2-hydroxy-3-phenylthiomethyl-4,7-diaza -5,8-dioxo-6-(carbamoylethyl)-9-amino-10-quinolin-1-yl]decyl benzamide;

[2R- (2R*, 3S*, 6S*, 9R*)]-N-t-butyl-2-[2-hydroxy-3-phenylmethyl-4,7-diaza -5,8-dioxo-6-(2-methylpropyl)-9-amino-10-indol-3 -yl]decyl benzamide;

[2R- (2R*, 3S*, 6S*, 9S*)]-N-t-butyl-2-[2-hydroxy-3-phenylmethyl-4,7-diaza -5,8-dioxo-6-(carbamoylmethyl)-9-amino-10-benzothien-2-yl]decyl benzamide;

[2R- (2R*, 3S*, 6S*, 9S*)]-N-t-butyl-2-[2-hydroxy-3-phenylmethyl-4,7-diaza -5,8-dioxo-6-(isopropyl)-9-amino-10-benzothien-2-yl]decyl benzamide;

[2R- (2R*, 3S*, 6S*, 9S*)]-N-t-butyl-2-[2-hydroxy-3-phenylmethyl-4,7-diaza -5,8-dioxo-6-(cyano)-9-amino-10-benzothien-3-yl]decyl benzamide;

[2R-(2R*, 3S*, 6S*, 9S*)]-N-t-butyl-2-[2-hydroxy-3-naphth-1-ylthiomethyl -4,7-diaza-5,8-dioxo-6-(cyano)-9-amino-10-benzothien-3-yl]decyl benzamide;

[2R- (2R*, 3S*, 6S*, 9S*)]-N-t-butyl-2-[2-hydroxy-3-phenylthiomethyl-4,7-diaza -5,8-dioxo-6-(isopropyl)-9-amino-10-benzothien-3-yl]decyl benzamide;

[2R- (2R*, 3S*, 6S*, 9S*)]-N-t-butyl-2-[2-hydroxy-3-phenylmethyl-4,7-diaza -5,8-dioxo-6-(carbamoylmethyl)-9-amino-10-benzothien-3-yl]decyl benzamide;

[2R- (2R*, 3S*, 6S*, 9R*)]-N-t-butyl-2-[2-hydroxy-3-naphthylmethyl-4,7-diaza -5,8-dioxo-6-(carboxymethyl)-9-amino-10-naphth-1-yl]decyl benzamide;

[2R-(2R*, 3S*, 6S*, 9R*)]-N-t -butyl-2-[2-hydroxy-3-naphthylmethyl-4,7 -diaza -5,8-dioxo-6-(carboxymethyl)-9-amino-10-indol-2-yl]decyl benzamide;

[2R-(2R*,3S*,6S*,9R*)]-N-t-butyl-2-[2-hydroxy-3-phenylthiomethyl-4,7-diaza -5,8-dioxo-6-(carbamoylmethyl)-9-N(t-butoxycarbonyl)amino-10-naphth-2-yl]decyl benzamide;

[2R-(2R*,3S*,6S*,9S*)]-N-t-butyl-2-[2-hydroxy-3-naphthylthiomethyl-4,7-diaza -5,8-dioxo-9-N-(t-butoxycarbonyl)amino-10-indol-3-yl]decyl benzamide;

[2R-(2R*,3S*,6S*,9S*)]-N-t-butyl-2-[2-hydroxy-3-phenylthiomethyl-4,7-diaza -5,8-dioxo-6-(thiolmethyl)-9-N(t-butoxycarbonyl)amino-10-phenyl]decyl benzamide;

[2R-(2R*,3S*,6S*,9R*)]-N-t-butyl-2-[2-hydroxy-3-phenylthiomethyl-4,7-diaza -5,8-dioxo-6-(carbamoylmethyl)-9-N(t-butoxycarbonyl)amino-9-naphth-1-yl]nonyl benzamide;

[2R-(2R*, 3S*,6S*,9R*)]-N-t-butyl-2-[2-hydroxy-3-phenylthiomethyl-4,7-diaza -5,8-dioxo-6-(1-methylpropyl)-9-N(t-butoxycarbonyl)amino-9-naphth-1-yl]nonyl benzamide;

[2R-(2R*,3S*,6S*,9S*)]-N-t-butyl-2-[2-hydroxy-3-naphthylmethyl-4,7-diaza -5,8-dioxo-6 -(imidazol-4-ylmethyl)-9-N(t-butoxycarbonyl)amino-9-indol-3-yl]nonyl benzamide;

[2R-(2R*,3S*,6S*,9S*)]-N-t -butyl-2-[2-hydroxy-3-phenylmethyl-4,7-diaza -5,8-dioxo-6-(imidazol-4-ylmethyl)-9-amino-9-naphth-2-yl]nonyl benzamide;

[2R-(2R*,3S*,6S*,9S*)]-N-t-butyl-2-[2-hydroxy-3-naphthylmethyl-4,7 -diaza -5,8-dioxo-6-(cyanomethyl)-9-N(t-butoxycarbonyl)amino-9-indol-3-yl]nonyl benzamide;

[2R- (2R*, 3S*, 6S*, 9S*)]-N-t-butyl-2-[2-hydroxy-3-naphthylmethyl-4,7-diaza -5,8-dioxo-6-(carboxymethyl)-9-N(t-butoxycarbonyl)amino-9-indol-3-yl]nonyl benzamide;

[2R- (2R*, 3S*, 6S*, 9S*)]-N-t-butyl-2-[2-hydroxy-3-phenylmethyl-4,7-diaza -5,8-dioxo-6-(hydroxymethyl)-9-N(ethoxycarbonyl)amino-9-naphth-1-yl]nonyl benzamide; and

[2R-(2R*, 3S*, 6S*, 9S*)]-N-t-butyl-2-[2-hydroxy-3-naphthylthiomethyl-4,7-diaza -5,8-dioxo-6-(1-hydroxyethyl)-9-N(propoxycarbonyl)amino-10-indol-3-yl]decyl benzamide; or
a pharmaceutically acceptable salt thereof.

The compounds of the present invention can be prepared according to the procedures shown below in Reaction Scheme I.

Reaction Scheme I:

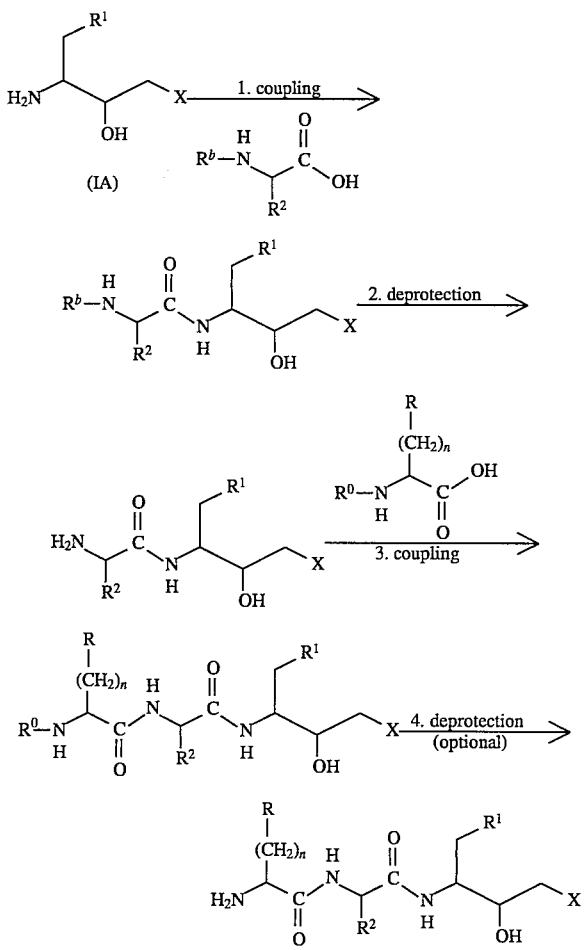

where:
R$^b$ is an amino-protecting group; and
R, R$^0$, R$^1$, R$^2$, n and X are as defined above for formula I.

Reaction Scheme I, above, is accomplished by carrying out reactions 1–4 in sequential order. Once a reaction is complete, the intermediate compound may be isolated, if desired, by procedures known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

Reaction 1.1 is a standard coupling reaction commonly employed in the synthesis of peptides which is carried out by reacting a appropriately substituted amine of formula IA, with an amino-protected amino acid reactant, in an aprotic solvent or mixture of solvents. The reaction is carried out in the presence or absence of a promoting agent preferably in the presence of a promoting agent, and in the presence of a coupling reagent. Typical aprotic solvents for this reaction are tetrahydrofuran and dimethyl formamide, preferably a mixture of such solvents. The reaction is carried out at a temperature from about −30° C. to about 25° C. The amine reactant is generally employed in equimolar proportions relative to the carboxylic acid reactant, in the presence of an equimolar quantity to a slight excess of the coupling reagent. Typical coupling reagents include the carbodiimides such as dicyclohexylcarbodiimide (DCC) and N,N'-diethylcarbodiimide; the imidazoles such as carbonyldiimidazole; as well as reagents such as bis(2-oxo-3-oxazolidinyl)phosphinic chloride (BOP-Cl) or N-ethoxycarbonyl-2-ethoxy-1,2-dihydroquinoline (EEDQ). A preferred coupling reagent for this reaction is DCC. A promoting agent is preferably included for this reaction; a preferred promoting agent is hydroxybenzotriazole hydrate (HOBT.H$_2$O).

Reaction I.2 is a standard amino deprotection reaction using procedures and methods known in the art. For example, the amino-protecting group, R$^b$, may be removed using a strong acid, preferably trifluoroacetic acid.

In Reaction I.3, the amine compound prepared in Reaction I.2 is coupled to a carboxylic acid reactant having the formula:

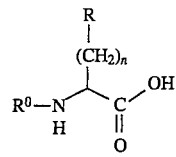

where n and R$^0$ are as defined above in formula I. Reaction I.3 is carried out substantially in accordance with the procedure detailed in Reaction I.1, above.

Reaction I.4 is an optional amino deprotection reaction carried out according to procedures and methods known in the art.

A person of ordinary skill in the art would be able to change the order of the reactions above, with proper use of amino- and carboxy-protecting groups. For example, a carboxy-protected amino acid such as that used in reaction I.1, above, can be coupled with a carboxylic acid reactant having the formula:

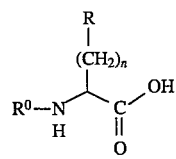

where n, R and R$^0$ are as defined above in formula I, substantially in accordance with the procedure detailed above. The resulting dipeptide compound is then deprotected before being coupled to the amine reactant, IA.

An alternative route to compounds of formula I can be obtained by coupling an amino-protected reactant having the structure

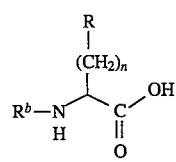

where:
n and R are as defined above in formula I; and
R$^b$ is an amino-protecting group; with the compound prepared in Reaction I.2, substantially according to the procedure detailed above, followed by amino-deprotection and then acylation with a suitable acyl halide, isocyanate or chloroformate, preferably in the presence of an acid scavenger such as a tertiary amine. A preferred acid scavenger is triethylamine. The acylation reaction is carried out at a temperature of from about −20° C. to about 25° C. Typical solvents for this reaction include ethers and chlorinated hydrocarbons, preferably diethyl ether, chloroform or methylene chloride.

The compounds of the formula IA where X is a group having the formula

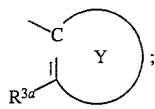

can be prepared according to the procedures shown below in Reaction Scheme A.

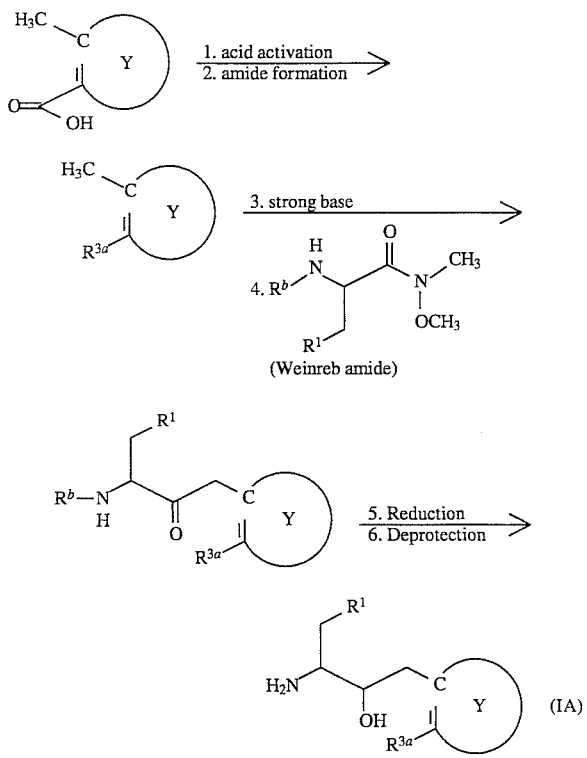

where:

$R^b$, $R^1$, $R^{3a}$ and Y are as defined above.

Reaction Scheme A, above, is accomplished by carrying out the above chemical reactions in sequential order. Once a reaction is complete, the intermediate compound may be isolated, if desired, by procedures known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

In Reaction A.1, the reaction is typically carried out by activating, that is, converting, a suitably substituted aryl, heterocycle or unsaturated heterocycle carboxylic acid to the corresponding acyl chloride or acyl bromide by reaction with thionyl chloride, thionyl bromide, phosphorous trichloride, phosphorous tribromide, phosphorous pentabromide or phosphorous pentachloride according to procedures and under conditions known in the art. Suitable aryl, heterocycle or unsaturated heterocycle carboxylic acid compounds are commercially available or prepared by procedures known in the art.

In Reaction A.2, the acyl chloride or acyl bromide, prepared from Reaction A.1, is reacted with ammonia or a primary or secondary amine having the formula

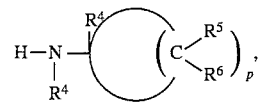

or

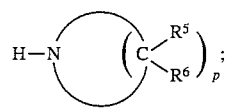

where $R^4$, $R^5$, $R^6$ and p are as defined above for formula I, in a nonpolar aprotic solvent or mixture of solvents in the presence or absence of an acid scavenger to afford the corresponding amide. The reaction is typically carried out at a temperature of from about −20° C. to about 25° C. Typical solvents for this reaction include ethers and chlorinated hydrocarbons, preferably diethyl ether, chloroform or methylene chloride. This reaction is preferably carried out in the presence of an acid scavenger such as a tertiary amine, preferably triethylamine.

In Reaction A.3, the amide prepared in Reaction A.2, is reacted with a strong base in the presence of a solubilizing agent to afford the corresponding anion which is then reacted in Reaction A.4 with an acylating agent, such as an Weinreb amide, to afford a ketone. Reaction A.3 is carried out in an aprotic solvent at a temperature of from about −78° C. to about 0° C. Typical bases used in Reaction A.3 include lithium amide bases and alkyl lithium bases, preferably $C_1$–$C_4$ alkyl lithium bases and lithium di($C_1$–$C_4$)alkylamide bases. Typical solubilizing agents for Reaction A.3 are tetramethyl($C_1$–$C_4$)alkylenediamines, preferably tetramethylethylenediamine. Reaction A.4 is carried out in an aprotic solvent at a temperature from about −80° C. to about −40° C. Typical solvents for Reactions A.3 and A.4 include ethers, preferably tetrahydrofuran. In Reaction A.4, the anion is generally employed in an amount ranging from about equimolar proportions to about a three molar excess of the anion, preferably in about a two molar excess of the anion relative to the Weinreb amide reactant.

In Reaction A.5, the ketone prepared in Reaction A.4 is reduced to the corresponding alcohol using a suitable reducing agent. The reaction is carried out in a protic solvent at a temperature of from about −25° C. to about 25° C. Typical reducing agents for this reaction include sodium borohydride, lithium borohydride, diisobutylaluminum hydride, and sodium bis(2-methoxyethoxy)aluminum hydride. A preferred reducing agent is sodium borohydride. Typical protic solvents for this reaction include alcohols, preferably ethanol.

Reaction A.6 is a standard amino deprotection reaction using procedures and methods known in the art to afford the corresponding amine of formula IA, which is then reacted in the coupling reaction I.1. The amine reactant, IA, may be reacted without purification, but it is preferably purified first.

The compounds of formula IA where X is a group having the structure

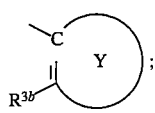

are prepared according to the procedures shown below in Reaction Scheme B.

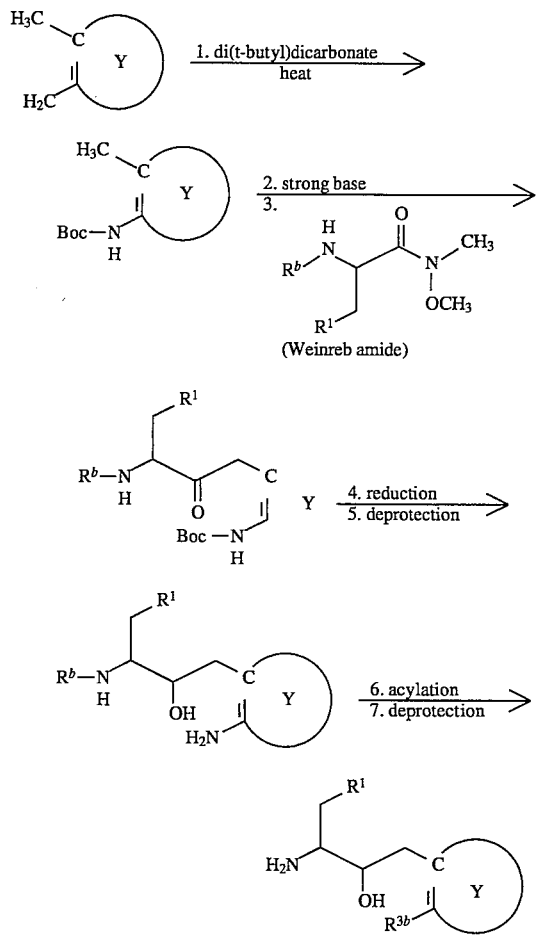

where:
$R^b$ $R^1$ Y and $R^{3b}$ are as defined above.

Reaction Scheme B, above, is accomplished by carrying out reactions 1–7 in sequential order. Once a reaction is complete, the intermediate compound may be isolated by procedures known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

In Reaction B.1, a suitably substituted aryl or unsaturated heterocycle amine is protected, under standard conditions used with amino-protecting groups known in the art. Reactions B.2 through B.5 are carried out substantially as described above in Reaction Scheme A.3– A.6, with the exception that in Reaction Scheme B, an additional deprotection reaction, Reaction B.5, is necessary to remove the amino-protecting group introduced in Reaction B.1. This is a standard amino deprotection reaction using procedures and methods known in the art. For example, the Boc group illustrated in Reaction Scheme B.1 may be removed using a strong acid, preferably trifluoroacetic acid.

In Reaction B.6, the illustrated intermediate is acylated with a suitable acyl halide, isocyanate or chloroformate, preferably in the presence of an acid scavenger such as a tertiary amine, preferably triethyl amine. The reaction is carried out at a temperature of from about −20° C. to about 25° C. Typical solvents for this reaction include ethers and chlorinated hydrocarbons, preferably diethyl ether, chloroform or methylene chloride.

Reaction B.7 is a standard amino deprotection reaction using procedures and methods known in the art to afford the corresponding amine having the formula IA, which is then reacted in Reaction 1.1, above. The amine reactant, IA, may be reacted without purification, but it is preferably purified first.

The compounds of formula I where X is a group having the structure:

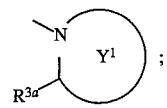

are prepared according to the procedures shown below in Reaction Scheme C.

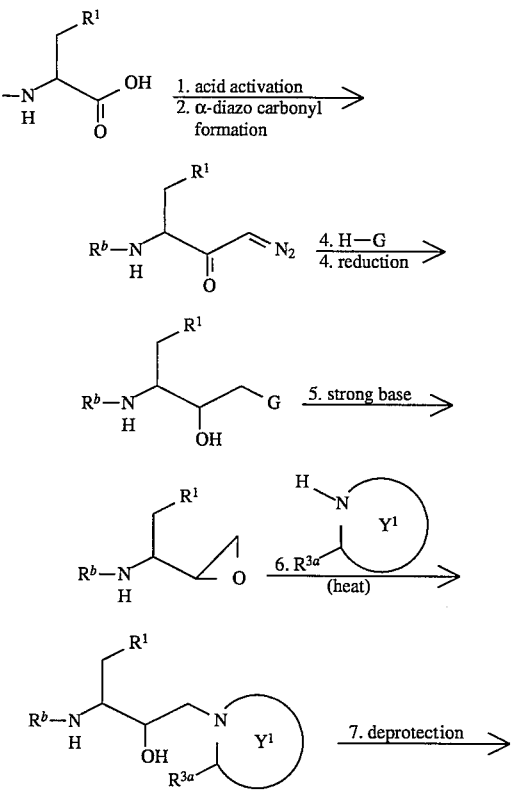

-continued
Reaction Scheme C

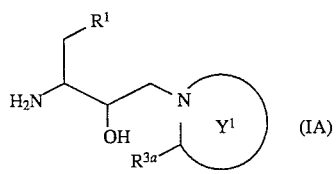

where:
R[1], R[3a] are as defined above for formula I;
R[b] is an amino-protecting group; and
G is halo.

Reaction Scheme C, above, is accomplished by carrying out reactions 1–7 in sequential order. Once a reaction is complete, the intermediate compound may be isolated, if desired, by procedures known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

Reaction C.1 is carried out by activating, that is, converting, an amino-protected carboxylic acid reactant having the structure:

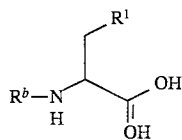

to the corresponding mixed anhydride under conditions known in the art. For example, the amino-protected carboxylic acid reactant may be reacted with a $C_1$–$C_6$ alkyl-chloroformate, such as isobutylchloroformate preferably in the presence of an acid scavenger. Preferred acid scavenges are the trialkylamines, preferably triethylamine. The reaction is typically carried out in an aprotic solvent such as ethyl acetate. Solvent choice is not critical so long as the solvent employed is inert to the ongoing reaction and the reactants are sufficiently solubilized to effect the desired reaction. The resulting mixed anhydride reactant is preferably used in Reaction C.2 without further isolation or purification.

Reaction C.2 is accomplished in two steps. First, a solution of sodium hydroxide, covered with a layer of an ether solvent, preferably diethyl ether, is reacted with a large excess of N-methyl-N-nitro-N-nitrosoguanidine to form a diazomethane reactant. The sodium hydroxide is preferably used as an aqueous solution having a concentration of about four to six mol/liter of sodium hydroxide. Once this reaction is substantially complete, the organic layer is dried over a dessicant such as potassium hydroxide. This solution is then reacted with the mixed anhydride from Reaction C.1, above, to form the corresponding α-diazo carbonyl compound. The diazomethane reactant is preferably used in this reaction without isolation or purification. The reaction is typically carried out at a temperature of from about −50° C. to about −20° C., preferably about −30° C.

In Reaction C.3, the α-diazo carbonyl compound prepared in Reaction C.2 is reacted with an acid of the formula H-G where G is halo, in an aprotic solvent such as diethylether to form an α-halo carbonyl compound. A preferred acid reactant is hydrochloric acid which provides the corresponding α-chloro carbonyl compound. A reaction is typically carried out at a temperature from about −30° C. to about 0° C. Solvent choice is not critical so long as the solvent employed is inert to the ongoing reaction and the reactants are sufficiently solubilized to effect the desired reaction. The acid reactant is typically added in the form of an anhydrous gas in small increments until the reaction appears substantially complete. The reaction can be monitored by thin layer chromatography.

In Reaction C.4, the carbonyl moietyl on the compound prepared in Reaction C.3 is reduced using standard conditions known in the art to form the corresponding α-chloro hydroxy compound. For example, the compound prepared in Reaction C.3 maybe combined with a reducing agent in a mixture of solvents. Typical reducing agents include sodium borohydride, lithium borohydride, zinc borohydride, diisobutylaluminum hydride and sodium bis(2-methoxyethoxy)aluminum hydride. A preferred reducing agent is sodium borohydride. Typical solvent mixtures include a protic and aprotic mixture such as tetrahydrofuran/water. Solvent choice is not critical so long as the solvent employed is inert to the ongoing reaction and the reactants are sufficiently solubilized to effect the desired reaction. The reaction is typically carried out at a temperature from about −10° C. to about 10° C., preferably about 0° C.

In Reaction C.5, the α-chloro hydroxy compound prepared in Reaction C.4 is treated with a strong base to form the corresponding epoxide under conditions known in the art. For example, the α-chloro hydroxy compound may be reacted with a potassium hydroxide/ethanol mixture in an organic solvent such as ethyl acetate. Solvent choice is not critical so long as the solvent employed is inert to the ongoing reaction and the reactants are sufficiently solubilized to effect the desired reaction. The reaction is typically carried out at a temperature from about 0° C to about the reflux temperature of the solvent. Preferably the reaction is carried out at room temperature.

In Reaction C.6, the epoxide prepared in Reaction C.5 is reacted with a compound of the formula

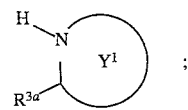

in a protic solvent at a temperature of from about 70° C. to 100° C. Solvent choice is not critical so long as the solvent employed is inert to the ongoing reaction and the reactants are sufficiently solubilized to effect the desired reaction. Typical solvents for this reaction include the alcohols, preferably ethanol. The reaction is preferably carried out at a temperature of about 80° C.

Reaction C.7 is a standard amino deprotection reaction using procedures and methods known in the art to afford the corresponding amine which is used in Reaction I.1, above.

The Weinreb amide used as a reactant in Reaction A.4 and B.3 maybe prepared by reacting an amino-protected amino acid with N-methoxy-N-methyl-amine in the presence of a promoting agent, an acid scavenger, and a coupling agent. The reaction is carried out in an aprotic solvent or mixture of solvents at a temperature of from about −25° C. to 25° C. A preferred promoting agent for this reaction is HOBT·$H_2O$. Preferred acid scavengers are tertiary alkylamines, preferably triethylamine or N-methylmorpholine. A preferred coupling reagent is ethyldimethylaminopropylcarbodiimide hydrochloride. The Weinreb amide afforded by this reaction is preferably isolated prior to its use in Reactions A.4 and B.3.

The compounds of formula IA, where $R^1$ is a group having the structure S-$R^{1x}$, where $R^{1x}$ is aryl or $C_5$–$C_7$ cylcoalkyl, are prepared using an Weinreb amide in Reactions A.4 and B.3, which has the following structure:

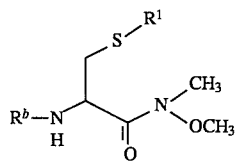

where:

$R^1$ and $R^b$ are as defined above.

This Weinreb amide may be prepared substantially in accordance with the reaction scheme described in Vederas et al., J. Am. Chem. Soc., 107, 7105–7109 (1985). In particular, this reaction scheme is carried out by first reacting amino-protected serine with triphenylphosphine, demethylazodicarboxylate (DMAD) or diethytazodicarboxylate (DEAD) in an aprotic solvent at a temperature of from about −80° C. to 0° C. to form the corresponding β-lactone. The reaction is typically carried out in an ether, such as tetrahydrofuran at a temperature of from about −80° C. to −50° C. Next, the lactone ring is opened to provide a compound having the structure:

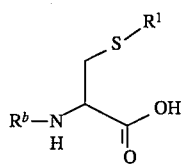

by reacting the lactone with an appropriately substituted thioanion having the structure, —S-$R^1$, where $R^1$ is as defined above for formula I. The thioanion compound is preferably formed by reacting the corresponding thiol with a strong base, such as sodium hydride or potassium hydride. This reaction is typically carried out in an aprotic solvent at a temperature from about 0° C. to about 40° C. and under an inert atmosphere, such as nitrogen. Typical solvents for this reaction include ethers, preferably tetrahydrofuran. The desired amide reactant is then formed by reacting the resulting carboxylic acid reactant with N-methoxy-N-methyl-amine in the presence of a promoting agent, an acid scavenger, and a coupling agent substantially as described above.

The heterocyclic reactants, used in Reaction C.6 above, of the formula

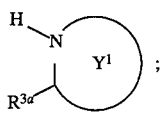

can be prepared using procedures and methods known in the art. For example, the heterocyclic reactants were typically prepared from the corresponding amino-protected amino acids by acid activation followed by treatment with an alkylamine. This reaction is typically carried out in the presence of an acid scavenger, such as N-methylmorpholine. Removal of the amino-protecting group using standard chemical deprotecting techniques then provided the heterocyclic reactants used above in Reaction C.8. Specifically, the [3S-(3R*,4aR*,8aR*)]-decahydroisoquinoline-3-N-t-butoxycarboxamide was prepared using (2S)-1,2,3,4-tetrahydro-3-isoquinolinecarboxylic acid by the following procedure:

1) amino-protection (t-Boc);
2) acid activation/reaction with t-butylamine;
3) catalytic hydrogenation;
4) amino-deprotection.

The carboxylic acid reactants used in the coupling reaction described in Reaction Scheme I.1, to the extent not commercially available, can be prepared using procedures known in the art.

It will be understood by those skilled in the art that in performing the processes described above it may be desirable to introduce chemical protecting groups into the reactants in order to prevent secondary reactions from taking place. Any amine, alkylamine or carboxy groups which may be present on the reactants may be protected using any standard amino- or carboxy-protecting group which does not adversely affect the remainder of the molecule's ability to react in the manner desired. Preferred amino-protecting groups are t-Boc and Cbz. A preferred carboxy-protecting group is benzhydryl. The various protective groups may then be removed simultaneously or successively using methods known in the art.

As noted above, all asymmetric forms, individual isomers and combinations thereof are considered part of this invention. Such isomers may be prepared from their respective precursors by the procedures described above, by resolving the racemic mixtures or by separating the dieasteromers. The resolution can be carried out in the presence of a resolving agent, by chromatography or by repeated crystallization or by some combination of these techniques which are known in the art. Further details regarding resolutions can be found in Jacques et al., Enantiomers, Racemates, and Resolutions, John Wiley & Sons 1981.

The compounds employed as initial starting materials in the synthesis of the compounds of this invention are known and, to the extent not commercially available are readily synthesized by standard procedures commonly employed in the art.

The pharmaceutically acceptable salts of the invention are typically formed by reacting a compound of formula I with an equimolar or excess amount of acid or base. The reactants are generally combined in a mutual solvent such as diethyl ether or benzene, for acid addition salts, or water or alcohols for base addition salts. The salts normally precipitate out of solution within about one hour to about ten days and can be isolated by filtration or other conventional methods.

The following Preparations and Examples further illustrate specific aspects of the present invention. It is to be understood, however, that these examples are included for illustrative purposes only and are not intended to limit the scope of the invention in any respect and should not be so construed.

In the following Preparations and Examples, the terms melting point, nuclear magnetic resonance spectra, electron impact mass spectra, field desorption mass spectra, fast atom bombardment mass spectra, infrared spectra, ultraviolet spectra, elemental analysis, high performance liquid chromatography, and thin layer chromatography are abbreviated "m.p.", "NMR", "EIMS", "MS (FD)", "MS (FAB)", "IR", "UV", "Analysis", "HPLC", and "TLC", respectively. In addition, the absorption maxima listed for the IR spectra are only those of interest and not all of the maxima observed.

In conjunction with the NMR spectra, the following abbreviations are used: "s" is singlet, "d" is doublet, "dd" is doublet of doublets, "t" is triplet, is quartet, "m" is multiplet, "dm" is a doublet of multipiers and "br.s", "br.d", "br.t", and "br.m" are broad singlet, doublet, triplet, and multiplet respectively. "J" indicates the coupling constant in Hertz (Hz). Unless otherwise noted, NMR data refers to the free base of the subject compound.

The NMR spectra were obtained on a Broker Corp. 270 MHz instrument or on a General Electric QE-300 300 MHz instrument. The chemical shifts are expressed in delta () δ values (parts per million downfield from tetramethylsilane). MS(FD) spectra were taken on a Varian-MAT 731 Spectrometer using carbon dendrite emitters. EIMS spectra were obtained on a CEC 21-110 instrument from Consolidated Electrodynamics Corporation. MS(FAB) spectra were obtained on a VG ZAB-3 Spectrometer. IR spectra were obtained on a Perkin-Elmer 281 instrument. UV spectra were obtained on a Cary 118 instrument. TLC was carried out on E. Merck silica gel plates. Melting points are uncorrected.

PREPARATION 1

A. N-t-Butyl-2-methylbenzamide

To a cold (0° C.) solution of 139.2 g (0.9 mol) of o-toluoyl chloride in 1200 mL of methylene chloride at 25° C., under nitrogen, was slowly added 180.0 g (1.8 mol) of triethylamine followed by the dropwise addition of a solution containing 73.14 g (1.0 mol) of t-butylamine in 200 mL of methylene chloride. The resulting reaction mixture was warmed to room temperature and allowed to react for 2.5 hours. The reaction mixture was then diluted with 1800 mL of water. The resulting organic and aqueous layers were separated, and the organic layer was washed sequentially with 2N sodium hydroxide, 1.0N hydrochloric acid and brine, dried over magnesium sulfate, filtered and then reduced to dryness under reduced pressure to provide 167.6 g of an off-white solid (mp 77°–78° C.).

Yield: 97%.

$^1$H NMR (CDCl$_3$): δ1.41 ( s, 9H), 2.41 ( s, 3H), 5.54 (br.s, 1H), 7.13–7.30 (m, 4H).

IR (CHCl$_3$): 3430, 3011, 2971, 2932, 1661, 1510, 1484, 1452, 1393, 1366, 1304, 1216, 876 cm$^{-1}$.

MS (FD): m/e 191 (M$^+$), 191 (100).

Analysis for C$_{12}$H$_{17}$NO: Calcd: C, 75.35; H, 8.76; N, 7.32; Found: C, 75.10; H, 9.11; N, 7.20.

B. (S)-N-C-Butyl-2-(3-(N-benzylcarbonyl)amino-2-oxo-4-phenylbutyl)benzamide

To a solution of 7.0 g (36.5 mmol) of the subtitled intermediate of Preparation 1A in 200 mL anhydrous tetrahydrofuran, was added 12.1 mL (80.3 mmol) N,N,N',N'-tetramethylethylenediamine (TMEDA) was added via syringe. The resulting solution was cooled to −78° C. and then 55.9 mL of sec-butyllithiumwas added dropwise via syringe while maintaining the temperature of the reaction under −60° C. The resulting reaction solution was then allowed to stir for approximately 1 hour at −78° C. before the addition of a solution containing 5.00 g (14.6 mmol) of (S)-N-methoxy-N-methyl-2-(N-Phenylmethyloxycarbonyl)amino-3-phenylpropanamide in 50 mL anhydrous tetrahydrofuran was added via cannula while maintaining the reaction temperature below −65° C. The resulting reaction mixture was warmed to −20° C., quenched using 20 mL saturated ammonium chloride and then diluted with 200 mL diethylether. The resulting layers were separated and the organic layer was washed sequentially with water, 0.2N sodiumhydrogensulfate and brine, dried over sodium sulfate, filtered and then reduced to dryness under reduced pressure to provide a colorless oil. This oil was purified using flash chromatography (eluent of 25% ethyl acetate in methylene chloride) to provide 6.08 g of a colorless foam.

Yield: 88%.

[a]D −289.26° (c 0.12, MeOH).

$^1$H NMR (CDCl$_3$) δ1.38 (s, 9H), 2.99 (dd, J=15; 6 Hz, 1H), 3.24 (dd, J=15; 6 Hz, 1H), 3.89 (d, J=18 Hz, 1H), 4.16 (d, J=! 8 Hz, 1H), 4.72 (dd, J=15, 6 Hz, 1H), 5.00–5.09 (m, 2H), 5.56 (d, J=6 Hz, 1H), 5.93 (br. s, 1H), 7.03–7.40 (m, 14H).

IR (CHCl$_3$): 3431, 3027, 3012, 2973, 1713, 1658, 1511, 1454, 1383, 1366, 1307, 1231, 1046 cm$^{-1}$.

MS (FD): m/e 472 (M$^+$), 218 (100).

Analysis for C$_{29}$H$_{32}$N$_2$O$_4$: Calcd: C, 73.70; H, 6.82; N, 5.93; Found: C, 73.41; H, 6.98; N, 5.83.

C. [2R-(2R*, 3S,)]-N-t-Butyl-2-(3-(N-benzylcarbonyl)amino-2-hydroxy-4-phenylbutyl)benzamide To a solution of 6.96 g (14.7 mmol) of the subtitled intermediate of Preparation 1B in 200 mL absolute ethanol, under nitrogen, was added 2.78 g (73.5 mmol) sodium borohydride. When the reaction was substantially complete, as indicated by TLC, the reaction mixture was diluted with 200 mL of ethyl acetate and quenched by the dropwise addition of 20 mL of saturated ammonium chloride. The organic and aqueous layers were then separated and the organic layer was washed sequentially with 1N hydrochloric acid, saturated sodium bicarbonate solution and brine, dried over sodium sulfate and then reduced to dryness under reduced pressure to provide 6.4 g of a colorless oil. Using $^1$H NMR, this oil was determined to be a 9:1 mixture of diastereomers. This oil was purified using flash chromatography (gradient eluent of 2–10% methylene chloride in ethyl acetate) to provide 5.12 g of the subtitled intermediate.

Yield: 74%.

[a]$_D$+10.38° (c 0.10, MeOH).

$^1$H NMR (CDCl$_3$): δ1.40 (s, 9H), 2.79 (dd, J=12; 3 Hz, 1H), 2.90–2.98 (m, 2H), 3.04 (44, J=12, 3 Hz, 1H), 3.70–3.81 (m, 1H), 3.97 (m, 1H), 4.96–5.08 (m, 2H), 5.10 (d, J=9 Hz, 1H), 5.88 (d, J=6 Hz, 1H), 5.93 (s, 1H), 7.13–7.42 (m, 14H).

IR (CHCl$_3$): 3431, 3028, 3012, 2971, 1773, 1643, 1515, 1454, 1367, 1229, 1028 cm$^{-1}$.

MS (FD): m/e 475 (M$^+$), 475 (100).

Analysis for C$_{29}$H$_{34}$N$_2$O$_4$: Calcd: C, 73.39; H, 7.22; N, 5.99; Found: C, 73.12; H, 7.48; N, 5.62.

D. [2R- (2R *, 3S*)]-N-t-Butyl-2-(3-amino-2-hydroxy-4-phenylbutyl)benzamide

A suspension was prepared containing 41.0 g (120 mmol) of the subtitled intermediate of Preparation 1C and 500 mg of 10% palladium on carbon in 150 mL absolute ethanol. This suspension was shaken under 60 psi hydrogen in a Parr shaker apparatus. The 10% palladium-on-carbon catalyst was then removed by filtration. The resultant filtrate was reduced to dryness under reduced pressure to provide 31.1 g of a light yellow foam. This foam was used without further purification.

Yield: 96%.

[a]$_D$+34.68° (c 1.0, MeOH).

$^1$H NMR (CDCl$_3$): δ1.46 (s, 9H), 2.71 (dd, J=13.7; 9.5 Hz, 1H), 2.84 (dd, J=13.3; 2.51 Hz, 1H), 2.95–3.06 (m, 2H), 3.23–3.29 (m, 1H), 3.84–3.90 (m, 1H), 6.23 (s, 1H), 7.19–7.37 (m, 12H) .

IR (CHCl$_3$): 3440, 3382, 3007, 2970, 2934, 1643, 1516, 1454, 1367, 1213 cm$^{-1}$.

MS (FD): m/e 341 (M$^+$), 341 (100).

EXAMPLE 1

A. [2R-(2R*, 3S*, 6S*)]-N-t-Butyl-2-[2-hydroxy-3-phenylmethyl-4-aza-5-oxo -6-N(t-butoxycarbonyl)amino-7-methyl]octyl benzamide To a cold (−23° C.) solution containing 1.34 g (6.18 mmol) of (S)-2-N-(t-butyloxycarbonyl)amino-3-methylbutanoic acid, 2.00 (5.88 mmol) of the subtitled intermediate of Preparation 1D and 0.833 g (6.18 mmol) of hydroxybenzotriazole hydrate (HOBT.H$_2$O) in 20 mL of tetrahydrofuran, under nitrogen, was added 1.24 g (6.00 mmol) of 1,3-dicyclohexylcarbodiimide (DCC). The resultant reaction mixture was slowly warmed to room temperature and then allowed to react overnight. The reaction mixture was then cooled to approximately 0° C., filtered, washed with ethyl acetate and then concentrated under reduced pressure to provide a residue. This residue was distributed between 150 mL of ethyl acetate and 25 mL of a saturated aqueous potassiumhydrogensulfate solution. The resulting layers were separated and the organic layer was washed sequentially with saturated solutions of sodium bicarbonate and brine, dried over magnesium sulfate, filtered and then reduced to dryness under reduced pressure to provide 3.95 g of a colorless foam. Half of this foam was purified using column chromatography (silicon dioxide; eluent of 3% methanol in chloroform) to provide 1.45 g of the desired subtitled compound. The other half of this foam was reacted according to the procedure detailed in Example 1B.

Analysis for C$_{31}$H$_{45}$N$_3$O$_5$: Calcd: C, 69.12; H, 8.23; N, 7.80; Found: C, 69.38; H, 8.43; N, 7.96.

B. [2R-(2R*,3S*,6S*)]-N-t-Butyl-2-[2-hydroxy-3-phenylmethyl-4-aza-5-oxo-6 -amino-7-methyl]octyl benzamide A solution of 2.0 g (max. 3.7 mmol) of the subtitled compound of Example 1A and 0.713 g (3.7 mmol) of toluenesulfonylhydroxide hydrate (TosOH.H$_2$O) in 75 mL of absolute ethanol was heated to 55° C. When the reaction was substantially complete, as indicated by TLC, the reaction mixture was cooled to room temperature and concentrated under reduced pressure to provide a residue. This residue was distributed between 100 mL of ethyl acetate and 50 mL of a 10% aqueous ammonium hydroxide solution. The resulting layers were separated and the organic layer was washed with brine, dried over magnesium sulfate, filtered and then reduced to dryness under reduced pressure to provide 1.0 g of a white foam. This foam was purified using flash chromatography (silicon dioxide, gradient eluent of 2–5% methanol in chloroform) to provide 0.97 of the desired subtitled compound.

Analysis for C$_{26}$H$_{37}$N$_3$O$_3$: Calcd: C, 71.04; H, 8.48; N, 9.56; Found: C, 70.85; H, 8.59; N, 9.56.

C. [2R-(2R*, 3S*, 6S*, 9S*)]-N-t-Butyl-2-[2-hydroxy-3-phenylmethyl -4,7-diaza-5,8-dioxo-6-(1-methylethyl)-9-N(t-butoxycarbonyl)amino-10-naphth-1-yl]decyl benzamide The desired subtitled compound was prepared substantially in accordance with the procedure detailed in Example 1A, using 226 mg (0.717 mmol) of (S)-2-N(t-butoxycarbonyl)amino-3-naphth-1-ylpropanoic acid, 300 mg (0.683 mmol) of the subtitled intermediate of Example 1B, 97 mg (0.71 mmol) of HOBT.H$_2$O and 144 mg (0.697 mmol) of DCC in 4 mL of tetrahydrofuran to provide 550 mg of material. This material was purified using flash chromatography (silicon dioxide, eluent of 1% methanol in chloroform) to provide 490 mg of an off-white foam.

Yield: 98%.

MS (FD): m/e 737 (M$^+$), 737 (100).

Analysis for C$_{44}$H$_{56}$N$_4$O$_6$: Calcd: C, 71.71; H, 7.66; N, 7.60; Found: C, 71.82; H, 7.73; N, 7.55.

EXAMPLE 2

[2R-(2R*,3S*,6S*,9R*)]-N-t-Butyl-2-[2-hydroxy-3-phenylmethyl-4,7-diaza -5,8-dioxo-6-(1-methylethyl)-9-N(t-butoxycarbonyl)amino-10-naphth-1-yl]decyl benzamide The desired titled compound was prepared substantially in accordance with the procedure detailed in Example 1A, using 226 mg (0.717 mmol) of (R)-2-N(t-butoxycarbonyl)amino-3-naphth-1-ylpropanoic acid, 300 mg (0.683 mmol) of the subtitled intermediate of Example 1B, 97 mg (0.71 mmol) of HOBT·H$_2$O and 144 mg (0.697 mmol) of DCC in 4 mL of tetrahydrofuran to provide 540 mg of a white foam. This foam was purified using flash chromatography (silicon dioxide, eluent of 1% methanol in chloroform) to provide 490 mg of an off-white foam.

Yield: 98%.

MS (FD): m/e 737 (M$^+$), 737 (100).

Analysis for C$_{44}$H$_{56}$N$_4$O$_6$: Calcd: C, 71.71; H, 7.66; N, 7.60; Found: C, 71.41; H, 7.90; N, 7.68.

EXAMPLE 3

[2R-(2R*, 3S*, 6S*, 9S*)]-N-t-Butyl-2-[2-hydroxy-3-phenylmethyl-5,8-dioxo -6-(1-methylethyl)-9-amino-10-naphth-1-yl]decyl benzamide A solution containing 3 mL of trifluoroacetic acid and 200 mg (0.271 mmol) of the subtitled compound of Example 1C in 20 mL of methylene chloride was allowed to react at ambient temperature. When the reaction was substantially complete, as indicated by TLC, the reaction mixture was basified using a saturated sodium bicarbonate solution. The resulting layers were separated and the organic layer was washed with an aqueous sodium chloride solution, dried over magnesium sulfate, filtered and then concentrated under reduced pressure to provide a foam. This foam was dissolved in a 5% ammonium hydroxide in methanol solution and allowed to stand overnight. The resultant mixture was then reduced to dryness under reduced pressure to provide a foam which was purified using flash chromatography (silicon dioxide; eluent of 5% methanol in chloroform) to provide 170 mg of the desired titled compound as a colorless foam.

Yield: 98%.

MS (FD): m/e 636 (M$^+$), 636 (100).

Analysis for C$_{39}$H$_{48}$N$_4$O$_4$: Calcd: C, 73.55; H, 7.60; N, 8.80; Found: C, 74.61; H, 7.73; N, 8.83.

EXAMPLE 4

[2R- (2R*, 3S*, 6S*, 9R*)]-N-t-Butyl-2-[2-hydroxy-3-phenylmethyl-4,7-diaza -2,8-dioxo-6-(1-methylethyl)-9-amino-10-naphth-1-yl] benzamide The desired titled compound was prepared substantially in accordance with the procedure detailed in Example 3, using 3 mL of trifluoroacetic acid and 200 mg (0.271 mmol) of the subtitled product of Example 2, in 20 mL of methylene chloride to provide 162 mg of a white foam. This foam was purified using flash chromatography (silicon dioxide, eluent of 1% methanol in chloroform) to provide 490 mg of an off-white foam.

Yield: 94%.

MS (FD): m/e 636 (M$^+$), 636 (100).

Analysis for C$_{39}$H$_{48}$N$_4$O$_4$: Calcd: C, 73.55; H, 7.60; N, 8.80; Found: C, 73.46; H, 7.75; N, 8.93.

EXAMPLE 5

A. [2R-(2R*, 3S*, 6S*)]-N-t-Butyl-2-[2-hydroxy-3-phenylmethyl-4-aza-5-oxo -6-N(benzyloxycarbonyl)amino-7-carbamoyl]heptyl benzamide The desired subtitled compound was prepared substantially in accordance with the procedure detailed in Example 1A, using 2.6 g (10 mmol) of (S)-2-N(benzyloxycarbonyl)amino-3-carbamoylpropanoic acid, 3.4 g (10 mmol) of the subtitled intermediate of Preparation 1D, 1.48 g (11 mmol) of HOBT-H$_2$O and 2.4 g (11 mmol) of DCC in 4 mL of tetrahydrofuran, with the exception that 1.09 mL (10 mmol) of N-methylmorpholine was also added to the reaction mixture, to provide 4.4 g of the desired subtitled compound.

Yield: 76%.

B. [2R-(2R*, 3S*, 6S*)]-N-t-Butyl-2-[2-hydroxy-3-phenylmethyl-4-aza-5-oxo -6-amino-7-carbamoyl]heptyl benzamide To a suspension of 0.5 g of 5% palladium-oncarbon in 95 mL of ethanol, was added 4 g (6.7 mmol) of the subtitled intermediate of Example 5A. The resulting reaction mixture was then stirred rapidly under 60 psi of hydrogen gas overnight at room temperature. When the reaction was complete, as determined by TLC, the 5% palladium-on-carbon was removed by filtration and the resulting solution was reduced to dryness under reduced pressure to provide 2.6 g of a solid. This solid was slurried in diethyl ether until substantially dissolved, and then concentrated under reduced pressure to provide a residue. This residue was recrystallized from an ethyl acetate/hexane mixture to provide 2.4 g of a solid.

Yield: 80%.

C. [2R-(2R*,3S*, 6S*,9R*)]-N-t-Butyl-2-[2-hydroxy-3-phenylmethyl-4,7-diaza -5,8-dioxo-6-(carbamoylmethyl)-9-N(t-butoxycarbonyl))amino-10-naphth-1-yl] decyl benzamide The desired subtitled compound was prepared substantially in accordance with the procedure detailed in Example 1, using 630 mg (2.0 mmol) of (R)-2-N(t-butoxycarbonyl)amino-3-naphth-1-ylpropanoic acid, 908 mg (2.0 mmol) of the subtitled compound of Example 5B, 283 mg (2.1 mmol) of HOBT.H$_2$O and 420 mg (2.04 mmol) of DCC in 40 mL of tetrahydrofuran to provide 1.50 g of material. This material was purified using flash chromatography (silicon dioxide; gradient eluent of 1.5–5% methanol in chloroform) to provide 920 mg of the desired subtitled compound.

Yield: 60%.

MS FD): m/e 751 (M$^+$), 751 (100).

Analysis for $C_{43}H_{53}N_5O_7$: Calcd: C, 68.69; H, 7.10; N, 9.31; Found: C, 68.66; H, 7.22; N, 9.27.

EXAMPLE 6

[2R-(2R*,3S*,6S*,9S*)]-N-t-Butyl-2-[2-hydroxy-3-phenylmethyl-4,7-diaza -5,8-dioxo-6-(carbamoylmethyl)-9-N(t-butoxycarbonyl)amino-10-naphth-1-yl]decyl benzamide The desired titled compound was prepared substantially in accordance with the procedure detailed in Example 1A, using 630 mg (2.0 mmol) of (S)-2-N(t-butoxycarbonyl)amino-3-naphth-1-ylpropanoic acid, 908 mg (2.0 mmol) of the subtitled compound of Example 5B, 283 mg (2.1 mmol) of HOBT.H$_2$O and 420 mg (2.04 mmol) of DCC in 40 mL of tetrahydrofuran to provide 1.37 g of material. This material was purified using flash chromatography (silicon dioxide; eluent of 2% methanol in chloroform) to provide 895 mg of the desired titled compound.

Yield: 60%.

MS (FD): m/e 751 (M$^+$), 751 (100).

Analysis for $C_{43}H_{53}N_5O_7$: Calcd: C, 68.69; H, 7.10; N, 9.31; Found: C, 68.58; H, 7.11; N, 9.01.

EXAMPLE 7

[2R- (2R*, 3S*, 6S*, 9S*)]-N-t-Butyl-2-[2-hydroxy-3-phenylmethyl-4,7-diaza -5,8-dioxo-6-(carbamoylmethyl)- 9-amino-10-naphth-1-yl]decyl benzamide The desired titled compound was prepared substantially in accordance with the procedure detailed in Example 3, using 3 mL of trifluoroacetic acid and 325 mg (0.432 mmol) of the titled compound of Example 6, in 20 mL of methylene chloride, with the exception that the foam isolated from the extraction procedure was not dissolved in a 5% ammonium hydroxide in methanol solution. The foam was purified using flash chromatography (silicon dioxide, eluent of 10% methanol in chloroform) to provide 248 mg of a white powder.

Yield: 88%.

MS (FD): m/e 652 (M$^+$), 652 (100).

Analysis for $C_{38}H_{45}N_5O_5$: Calcd: C, 70.13; H, 6.81; N, 10.76; Found: C, 70.32; H, 7.05; N, 10.71.

EXAMPLE 8

[2R-(3R*,3S*,6S*,9R*)]-N-t-Butyl-2-[2-hydroxy-3-phenylmethyl-4,7-diaza -5,8,dioxo-6-(carbamoylmethyl)-9-amino-10-naphth-1-yl]decyl benzamide The desired titled compound was prepared substantially in accordance with the procedure detailed in Example 3, using 3 mL of trifluoroacetic acid and 325 mg (0.432 mmol) of the subtitled compound of Example 5C, in 20 mL of methylene chloride to provide a white foam. This foam was purified using flash chromatography (silicon dioxide, eluent of 7% methanol in chloroform) to provide 280 mg of a white foam.

Yield: 100%.

Analysis for $C_{39}H_{48}N_4O_4$: Calcd: C, 70.13; H, 6.81; N, 10.76; Found: C, 70.38; H, 7.01; N, 10.79.

EXAMPLE 9

[2R-(2R*, 3S*, 6S*, 9S*)]-N-t-Butyl-2-[2-hydroxy-3-phenylmethyl-4,7-diaza -5,8-dioxo-6-(carbamoylmethyl)-9-N(t-butoxycarbonyl)amino-10-phenyl]decyl benzamide The titled compound was prepared substantially in accordance with the procedure detailed in Example 1A, using 132.6 mg (0.5 mmol) of (S)-2-N(t-butoxycarbonyl)amino-3-phenylpropanoic acid and 227 mg (0.5 mmol) of the subtitled compound of Example 5B and using 81 mg (0.5 mmol) of carbonyldiimidazole as the coupling agent, in 40 mL of methylene chloride to provide 130 mg of the desired titled compound.

Yield: 38%.

Analysis for $C_{39}H_{51}N_5O_7$: Calcd: C, 66.74; H, 7.32; N, 9.98; Found: C, 65.59; H, 7.44; N, 9.76.

EXAMPLE 10

[2R- (2R*, 3S*, 6S*, 9R* )]-N-t-Butyl-2-[2-hydroxy-3-phenylmethyl-4,7-diaza -5,8-dioxo-6-(carbamoylmethyl)-9-N(t-butoxycarbonyl)amino-10-phenyl]decyl benzamide The titled compound was prepared substantially in accordance with the procedure detailed in Example 9, using 136 mg (0.5 mmol) of (R)-2-N(t-butoxycarbonyl)amino-3-phenylpropanoic acid, 227 mg (0.5 mmol) of the subtitled compound of Example 5B and 81 mg (0.5 mmol) of carbonyldiimidazole, in 40 mL of methylene chloride to provide 100 mg of the desired titled compound.

Yield: 29%.

EXAMPLE 11

A. [2R-(2R*,3S*,6S*)]-N-t-Butyl-2-[2-hydroxy-3-phenylmethyl-4-aza-5-oxo -6-N(benzylcarbonyl)amino-7-imidazol-4-yl]heptyl benzamide The desired subtitled compound was prepared substantially in accordance with the procedure detailed in Example 1A, using 1.79 g (6.18 mmol) of (S)-2-N(benzyloxycarbonyl)amino-3-imidazol-4-ylpropanoic acid, 2.00 g (5.88 mmol) of the subtitled intermediate of Preparation 1D, 0.83 g (5.18 mmol) of HOBT·H$_2$O and 1.24 g (6.00 mmol) of DCC in 25 mL of tetrahydrofuran containing 2.5 mL of dimethylformamide, with the exception that the reaction was carried out at ambient temperature. The resultant material was isolated using flash chromatography (silicon dioxide; eluent of 3% methanol in chloroform) to provide 3.46 g of an off-white foam. This foam was used without further purification.

Yield: 96%.

Analysis for C$_{35}$H$_{41}$N$_5$O$_5$: Calcd: C, 68.72; H, 6.76; N, 11.45; Found: C, 65.60; H, 6.61; N, 10.94.

B. [2R-(2R*, 3S*, 6S*)]-N-t-Butyl-2-[2-hydroxy-3-phenylmethyl-4-aza-5-oxo -6-amino-7-imidazol-4-yl]heptyl benzamide To a suspension of 1.9 g of 5% palladium-oncarbon in 65 mL of ethanol, was added 3.36 g (5.5 mol) of the subtitled intermediate of Example 11A. The mixture was then stirred rapidly under hydrogen for approximately 3 ½ hours. When the reaction was complete, as determined by TLC, the 5% palladium-on-carbon was removed by filtration and the resulting solution was reduced to dryness under reduced pressure to provide an oil which became a chalky solid when exposed to air. This solid was dissolved in a 5:1 water/saturated potassiumhydrogen sulfate solution then washed with ethyl acetate, degassed and basified to pH 9 using a 5M solution of ammonium hydroxide. This solution was then diluted using 50 mL of ethyl acetate and the resultant layers were separated, the organic layer dried over magnesium sulfate, filtered and then concentrated under reduced pressure to provide the desired subtitled compound as a pale yellow foam.

Analysis for C$_{27}$H$_{35}$N$_5$O$_3$: Calcd: C, 67.90; H, 7.39; N, 14.66; Found: C, 67.94; H, 7.50; N, 14.36.

MS: m/e 478 (M$^+$).

C. [2R-(2R*,3S*,6S*,9S*)]-N-t-Butyl-2-[2-hydroxy-3-phenylmethyl-4,7-diaza -5,8-dioxo-6-(imidazol-4-ylmethyl)-9-N(t-butoxycarbonyl)amino-10-naphth-1 -yl] decyl benzamide The desired subtitled compound was prepared substantially in accordance with the procedure detailed in Example 1A, using 330 mg (1.05 mmol) of (S)-2-N(t-butoxycarbonyl)amino-3-naphth-1-ylpropanoic acid, 500 mg (1.05 mmol) of the subtitled compound of Example 11B, 149 mg (1.10 mmol) of HOBT·H$_2$O and 221 mg (1.07 mmol) of DCC in 20 mL of tetrahydrofuran to provide 1.03 g of an oil. This oil was purified using flash chromatography (silicon dioxide; gradient eluent of 3–10% methanol in chloroform) to provide 612 mg of the desired subtitled compound.

Yield: 76%.

MS (FD): m/e 774 (M$^+$), 774 (100).

Analysis for C$_{45}$H$_{54}$N$_6$O$_6$: Calcd: C, 69.74; H, 7.02; N, 10.84; Found: C, 69.55; H, 6.86; N, 10.57.

EXAMPLE 12

[2R-(2R*,3S*,6S*,9R*)]-N-t-Butyl-2-[2-hydroxy-3-phenylmethyl-4,7-diaza -5,8-dioxo-6-(imidazol-4-ylmethyl)-9-N(t-butoxycarbonyl)amino-10-naphth-1-yl] decyl benzamide The desired titled compound was prepared substantially in accordance with the procedure detailed in Example 1A, using 330 mg (1.05 mmol) of (R)-2-N(t-butoxycarbonyl)amino-3-naphth-1-ylpropanoic acid, 500 mg (1.05 mmol) of the subtitled compound of Example 11B, 149 mg (1.10 mmol) of HOBT·H$_2$O and 221 mg (1.07 mmol) of DCC in 20 mL of tetrahydrofuran to provide 1.03 g of an oil. This oil was purified using flash chromatography (silicon dioxide; gradient eluent of 3–10% methanol in chloroform) to provide 612 mg of the desired titled compound.

Yield: 76%.

MS (FD): m/e 774 (M$^+$), 774 (100).

Analysis for C$_{45}$H$_{54}$N$_6$O$_6$: Calcd: C, 69.74; H, 7.02; N, 10.84; Found: C, 69.75; H, 6.98; N, 10.88.

EXAMPLE 13

[2R-(2R*,3S*, 6R*,9S*)]-N-t-Butyl-2-[2-hydroxy-3-phenylmethyl-4,7-diaza -5,8-dioxo-6-(carbamoylmethyl)-9-N(t-butoxycarbonyl)amino-10-naphth-1-yl] decyl benzamide The desired titled compound was prepared substantially in accordance with the procedure detailed in Example 1A, using 79 mg (0.50 mmol) of (S)-2-N(t-butoxycarbonyl)amino-3-naphth-1-ylpropanoic acid, 114 mg (0.50 mmol) of the subtitled compound of Example 5B, 35.0 mg (0.525 mmol) of HOBT·H$_2$O and 51.6 mg (0.50 mmol) of DCC in 3 mL of tetrahydrofuran to provide 177 mg of a solid. This solid was purified to provide 77 mg of a white solid.

Yield: 76%.

MS (FD): 751 (M$^+$), 751 (100).

Analysis for C$_{43}$H$_{53}$N$_5$O$_7$: Calcd: C, 68.69; H, 7.10; N, 9.31; Found: C, 68.74; H, 7.10; N, 9.15.

EXAMPLE 14

[2R-(2R*, 3S*, 6S*, 9S*)]-N-t-Butyl-2-[2-hydroxy-3-phenylmethyl-4,7-diaza -5,8-dioxo-6-(carbamoylmethyl)-9-N(t-butoxycarbonyl)amino-10-indol-3-yl]decyl benzamide The desired titled compound was prepared substantially in accordance with the procedure detailed in Example 1A, using 84 mg (0.276 mmol) of (S)-2-N(t-butoxycarbonyl)amino-3-indol-3-ylpropanoic acid, 125 mg (0.275 mmol) of the subtitled compound of Example 5B, 38 mg (0.281 mmol) of HOBT·H$_2$O and 57 mg (0.276 mmol) of DCC in mL of tetrahydrofuran. The desired titled compound was purified using flash chromatography (gradient eluent of 3–10% methanol in methylene chloride) to provide 177 mg of a white foam/solid.

Yield: 87%.

$^1$H NMR (d$_6$-DMSO) δ1.29 (s, 9H), 1.36 (s, 9H), 40 (d, J=4.8 Hz, 2H), 60–2.65 (m, 2H), 2.82–3.09 (m, 4H), 3.57–3.61 (m, 1H), 3.79–3.82 (m, 1H), 4.14–4.18 (m, 1H), 4.40–4.47 (m, 1H), 5.88 (d, J=5.3 Hz, 1H), 6.92–6.97 (m, 3H), 7.02–7.10 (m, 2H), 7.14–7.19 (m, 6H), 7.23–7.32 (m, 5H), 7.55 (d, J=7.8 Hz, 1H), 7.64 (d, J=8.8 Hz, 1H), 8.16 (d, 1H), 8.24 (s, 1H), 10.78 (s, 1H).

MS ( FD ): m/e 740 (M$^+$-1), (100).

Analysis for C$_{41}$H$_{52}$N$_6$O$_7$·0.3EtOAc: Calcd: C, 66.06; H, 7.15; N, 10.95; Found: C, 66.08; H, 7.15; N, 10.93.

EXAMPLE 15

[2R- (2R*, 3S*, 6S*, 9R*)]-N-t-Butyl-3-[2-hydroxy-3-phenylmethyl-4,7-diaza -5,8-dioxo-6-(carbamoylmethyl)-9-N(t-butoxycarbonyl)amino-10-indol-3-yl]decyl benzamide The desired titled compound was prepared substantially in accordance with the procedure detailed in Example 1A, using 84 mg (0.276 mmol) of (R)-2-N(t-butoxycarbonyl)amino-3-indol-3-ylpropanoic acid, 125 mg (0.275 mmol) of the subtitled compound of Example 5B, 38 mg (0.281 mmol) of HOBT.H$_2$O and 57 mg (0.276 mmol) of DCC in mL of tetrahydrofuran. The desired titled compound was purified using flash chromatography (gradient eluent 3–10% methanol in methylene chloride ) to provide 195 mg of a white foam/solid.

Yield: 96%.

$^1$H NMR (d$_6$-DMSO) δ1.30 (s, 9H), 1.36 (s, 9H), 2.30–2.39 (m, 2H), 2.59–2.67 (m, 2H), 2.86–2.94 (m, 2H), 3.03–3.10 (m, 2H), 3.56–3.60 (m, 1H), 3.80–3.84 (m, 1H), 4.13–4.17 (m, 1H), 4.44–4.48 (m, 1H), 5.91 (d, J=5.3 Hz, 1H), 6.80 (d, J=7.2 Hz, 1H), 6.88 (s, 1H), 6.95 (t, 7.2 Hz, 1H), 7.03 (t, J=7.6 Hz, 1H ), 7.09–7.35 (m, 12H), 7.53–7.59 (m, 2H), 8.24–8.26 (m, 2H), 10.77 (s, 1H).

MS ( FD ): m/e 741 (M$^+$), (41), 740 (100).

Analysis for C$_{41}$H$_{52}$N$_6$O$_7$.H$_2$O: Calcd: C, 64.89; H, 7.17; N, 11.07; Found: C, 64.69; H, 6.89; N, 10.95.

EXAMPLE 16

[2R- (2R*, 3S*, 6S*, 9S*)]-N-t-Butyl-2-[2-hydroxy-3-phenylmethyl-4,7-diaza -5,8-dioxo-6-(carbamoylmethyl)-9-N(t-butoxycarbonyl)amino-9-phenyl]nonyl benzamide To a solution containing 125.6 mg (0.5 mmol) of (S)-2-N-(t-butoxycarbonyl)amino-2-phenylethanoic acid and 81 mg (0.5 mmol) of carbonyldiimidazole in 20 mL of methylene chloride, was added 227 mg (0.5 mmol) of the subtitled intermediate of Preparation 1D. The resultant reaction mixture was reacted at room temperature overnight and then was concentrated under reduced pressure while heating (35° C.) to provide an amorphous solid. This solid was redissolved in 125 mL of a 4:1 ethyl acetate/water mixture. The resulting layers were separated and the organic layer was washed sequentially with a saturated sodium bicarbonate solution, a 5% aqueous citric acid solution, a second saturated sodium bicarbonate solution and brine. The resultant solution was dried over magnesium sulfate, filtered and then reduced to dryness under reduced pressure to provide a residue. This residue was slurried with diethyl ether, filtered and then reduced to dryness under reduced pressure to provide 181 mg of material. This material was purified using high performance liquid chromatography (HPLC) (55% acetonitrile/44% water/1% acetic acid) to provide 90 mg of the desired titled compound.

Yield: 26%.

Analysis for C$_{38}$H$_{49}$N$_5$O$_7$. Calcd: C, 66.36; H, 7.18; N, 10.18; Found: C, 65.63; H, 7.10; N, 10.28.

EXAMPLE 17

[2R- (2R*, 3S*, 6S*, 9R*)]-N-t-butyl-2-[2-hydroxy-3-phenylmethyl-4,7-diaza 5,8-dioxo-6-(carbamoylmethyl)-9-N(t-butoxycarbonyl)amino-9-phenyl]nonyl benzamide The desired titled compound was prepared substantially in accordance with the procedure detailed in Example 16, using 630 mg (2.0 mmol) of (R)-2-N(t-butoxycarbonyl)amino-2-phenylethanoic acid, 454 mg (1 mmol) of the subtitled intermediate of Preparation 1D, 162 mg (1 mmol) of carbonyldiimidazole in 30 mL of methylene chloride to provide 425 mg of material. This material was purified using HPLC (55% acetonitrile/44% water/1% acetic acid) to provide 285 mg of the desired titled compound.

Yield: 38%.

Analysis for C$_{38}$H$_{49}$N$_5$O$_7$. Calcd: C, 66.36; H, 7.18; N, 10.18; Found: C, 66.20; H, 7.23; N, 10.31.

As noted above, the compounds of the present invention are useful for inhibiting HIV protease, which is an enzyme associated with viral component production and assembly. An embodiment of the present invention is a method of treating or preventing HIV infection comprising administering to a primate in need thereof an effective amount of a compound of formula I or a pharmaceutically acceptable salt thereof. Another embodiment of the present invention is a method of treating or preventing AIDS comprising administering to a primate in need thereof an effective amount of a compound of formula I or a pharmaceutically acceptable salt thereof. A further embodiment of the present invention is a method of inhibiting HIV replication comprising administering to an HIV infected cell, a cell susceptible to HIV infection or a primate in need thereof, an effective amount of a compound of formula I or a pharmaceutically acceptable salt thereof.

The term "effective amount" as used herein, means an amount of a compound of formula I which is capable of inhibiting the HIV protease mediated viral component production and assembly. The HIV protease inhibition contemplated by the present method includes either therapeutic or prophylactic treatment, as appropriate. The specific dose of compound administered according to this invention to obtain therapeutic and/or prophylactic effects will, of course, be determined by the particular circumstances surrounding the case, including, for example, the compound administered, the route of administration, the condition being treated and the individual being treated. A typical daily dose will contain a dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg.

The compounds can be administered by a variety of routes including oral, rectal, transdermal, subcutaneous, intravenous, intramuscular and intranasal. The compounds of the present invention are preferably formulated prior to administration. Therefore, another embodiment of the present invention is a pharmaceutical formulation comprising an effective amount of a compound of formula I or a pharmaceutically acceptable salt thereof and a pharmaceutically acceptable carrier, diluent or excipient therefor.

The active ingredient in such formulations comprises from 0.1% to 99.9% by weight of the formulation. By "pharmaceutically acceptable" it is meant that the carrier, diluent or excipient is compatible with the other ingredients of the formulation and not deleterious to the recipient thereof.

The present pharmaceutical formulations are prepared by known procedures using known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

The following formulation examples are illustrative only and are not intended to limit the scope of the invention in any way. The term "active ingredient" means a compound according to formula I or a pharmaceutically acceptable salt thereof.

Formulation 1

Hard gelatin capsules are prepared using the following ingredients:

|  | Quantity (mg/capsule) |
|---|---|
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
|---|---|
| Active ingredient | 0.25 |
| Methanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

|  | Quantity (mg/tablet) |
|---|---|
| Active ingredient | 60 |
| Starch | 45 |
| Microcrystalline cellulose | 35 |
| Polyvinylpyrrolidone (as 10% solution in water) | 4 |
| Sodium carboxymethyl starch | 4.5 |
| Magnesium stearate | 0.5 |
| Talc | 1 |
| Total | 150 |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

|  | Quantity (mg/capsule) |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 mL dose, are made as follows:

| | |
|---|---|
| Active ingredient | 50 mg |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| Active ingredient | 100 mg |
| Isotonic saline | 1,000 mL |

The solution of the above ingredients generally is administered intravenously to a subject at a rate of 1 mL per minute.

The following experiment (Fluorescence HIV-1 Protease Inhibitor Assay) was carried out to demonstrate the ability of the compounds of formula I to inhibit HIV protease.

As used herein, the abbreviations are defined as follows:

BSA — bovine serum albumin BOC — t-butyloxycarbonyl BrZ — 2-bromobenzyloxycarbonyl 2-ClZ-2-chlorobenzyloxycarbonyl DCC — dicyclohexylcarbodiimide DIEA — diisopropylethylamine DTT — dithiothreitol EDTA — ethylenediaminetetraacetic acid FITC — fluorescein isothiocarbamyl HEPES — 4-(2-hydroxyethyl)-1-piperazineethanesulfonic acid MES — 4 morpholineethanesulfonic acid PAM — phenylacetimidomethyl TAPS — 3-[tris(hydroxymethyl)methyl]amino-1-sulfonic acid TRIS — tris(hydroxymethyl)aminomethane TOS — p-toluenesulfonyl (tosyl)

I. Preparation of Protease and Gag Fractions

A. Culture of E. coli K12 L507/pHP10D

Lyophils of *E. coli* K12 L507/pHP10D were obtained from the Northern Regional Research Laboratory, Peoria, Ill. 61604, under the accession number NRRL B-18560 (deposited Nov. 14, 1989). The lyophils were decanted into tubes containing 10 mL LB medium (10 g Bactotryprone, 5 g Bacto-yeast extract, and 10 g sodium chloride per liter; the pH was adjusted to 7.5 and incubated at 32° C., overnight).

A small portion of the overnight culture was placed on LB-agar (LB medium with 15 g/L Bacto-agar) plates containing 12.5 µg/mL tetracycline in a manner so as to obtain a single colony isolate of *E. coli* K12 L507/pHP10D. The single colony obtained was inoculated into 10 mL of LB medium containing 12.5 µg/mL tetracycline and incubated overnight at 32° C. with vigorous shaking. The 10 mL overnight culture was inoculated into LB medium containing 12.5 µg/mL tetracycline and incubated at 32° C. with vigorous shaking until the culture reached mid-log phase.

B. Culture of *E. coli* K12 L507/pHGAG

Lyophils of *E. coli* K12 L507/pHGAG were obtained from the NRRL under the accession number NRRL B-18561 (deposited Nov. 14, 1989). A purified colony of *E. coli* K 12 L507/pHGAG was isolated, and used as an inoculum for a culture which was grown to mid-log phase in substantial accordance with the teaching of Step A, above, for *E. coli* K12 L507/pHP10D.

C. Preparation of Protease Fraction

A culture of *E. coli* K12 L507/pHP10D was grown to mid-log phase at 32° C. in LB media containing 12.5 µg/ml tetracycline. The cultivation temperature was quickly elevated to 40° C. to induce gene expression, and the cells were allowed to grow for 2.5 hours at this temperature before the culture was quickly chilled on ice. The cells were centrifuged and the cell pellet was resuspended in 20 mL 50 mmol MES buffer (pH 6.0) containing 1 mmol EDTA, 1 mmol DTT, 1 mmol PMSF and 10% glycerol ("Buffer A"). Cells were lysed by sonication using a Fischer Model 300 Dismembrator and a microtip probe. Following centrifugation at 27,000 x g, the supernatant was diluted to a total volume of 60 mL with Buffer A and loaded onto a 2.0×19 cm QAE-Sepharose column (1 mL/min, 4° C.), that had been equilibrated in Buffer A. The column was washed isocratically for 180 min and then eluted with a gradient eluent of 0–1.0M sodium chloride in Buffer A over 120 min. Enzymatic activity was measured by HPLC using the synthetic peptide SQNYPIV as described in Margolin et al., *Biochem. Biophys. Res. Commun.*, 167, 554–560 (1990); the production of the p1 peptide (SQNY) was measured.

The active fractions were combined, made 1.2M in ammonium sulfate, and applied to a 2.0×18 cm hexyl agarose column that had been equilibrated in Buffer A containing 1.2M ammonium sulfate. The sample was loaded at a flow rate of 1 mL/min at 4° C., washed with the equilibration buffer for 240 min (1 mL/min) and then eluted using a reverse linear gradient of 1.2–0M ammonium sulfate in Buffer A for 120 min at the same flow rate. The column was then washed isocratically in Buffer A for 120 min.

The active fractions were combined, concentrated to 10 mL using an Amicon stirred cell with a YM-10 membrane and then applied to a MonoS cation exchange column (1.0×10 cm) that had been equilibrated in Buffer A. The sample was loaded at a flow rate of 1 mL/min at 25° C. After washing isocratically for 30 min, the protease was eluted using a linear gradient of 0–0.45M sodium chloride in Buffer A over 40 min.. The column was washed isocratically in Buffer A containing 0.45M aqueous sodium chloride for 30 min.

The active fractions were combined and concentrated to 200 µL using an Amicon stirred cell and a YM-10 membrane and then the protease was applied to a Superose 6 size exclusion column equilibrated in Buffer A containing 0.1M aqueous sodium chloride. The column was washed isocratically in this buffer at a flow rate of 0.5 mL/min, following which the HIV protease was eluted as a single peak.

QAE-Sepharose, and hexyl agarose were purchased from Sigma Chemical Company. Superose 6 and MonoS were were purchased from Pharmacia. Buffers and reagents were obtained from Sigma.

D. Preparation of Gag Fraction

In an analogous manner, a culture of *E. coli* K12 507/pHGAG was grown to mid-log phase at 32° C. then shifted to 40° C. for about 4 to 5 hours. The culture was chilled on ice and centrifuged, then the pellet was resuspended in 8 mL lysis buffer containing 5 mg/mL lysozyme. Lysis buffer was comprised of 50 mM Tris-HCl (pH 7.8), 5 mM EDTA, 1 mM DTT, 100 mM NaCl, 1 µg/mL E64 and 2 µg/mL aprotinin. The culture was incubated about 30 to 60 minutes at 4° C., then briefly sonicated in a Branson® Cell Disrupter at 60% power, for three 20 second bursts with chilling between each burst. The culture was then centrifuged at 15,000 x g. The supernatant, which contains the unprocessed gag protein, was partially purified by size exclusion chromatography on a Sephadex G-50 column and stored at −20° C. in 50% glycerol and lysis buffer.

II. Preparation of Substrate: $N^\alpha$-Biotin-Gly-Ser-Gln-Asn-Tyr-Pro-Ile-Val-Gly-Lys(Nε-FITC)-OH A. Preparation of $N^\alpha$-Biotin-Gly-Ser-Gln-Asn-Tyr-Pro-Ile-Val-Gly-Lys-OH The protected peptide-resin $N^\alpha$-Boc-Gly-Ser-Gln-Asn-Tyr(BrZ)-Pro-Ile-Val-Gly-Lys(2-ClZ)-OCH$_2$-PAM-resin was synthesized on an Advanced Chemtech Model 200 peptide synthesizer at 1.5 mmol scale using the standard double-couple protocol. The amino terminal Boc group was removed with 50% trifluoroacetic acid in methylene chloride and the resulting resin neutralized with 5% diisopropylethylamine (DIEA) in methylene chloride. Then, 1.1 g (4.5 mmol) of biotin in 20 mL of dimethyl sulfoxide was added to the peptide resin, followed by 4.5 mmol of dicyclohexylcarbodiimide (DCC) in 9 mL of methylene chloride. The resulting reaction mixture was diluted to 40 mL total volume using 11 mL methylene chloride, and then allowed to react for approximately 5 hours. The reaction solution was concentrated, the resin washed sequentially with dimethylsulfoxide, dimethylformamide and methylene chloride and then neutralized with 5% DIEA in methylene chloride. This reaction was repeated twice, with the reaction time being extended to 12 hours per reaction. Ninhydrin analysis of the resin indicated complete reaction of the biotin with the glycine amine group. The final peptide resin was washed extensively with dimethylformamide and methylene chloride and dried to provide 4.3 g (98%).

B. Deprotection

The peptide was deprotected and cleaved from the resin using 50 mL of a hydrofluoric acid/m-cresol solution, 0° C., 1 hour. After removal of the hydrofluoric acid by vacuum distillation, the m-cresol was extracted from the reaction mixture using 100 mL diethylether. The peptide was then solubilized in 50% aqueous acetic acid, frozen and lyophilized to provide 2.14 g.

C. Purification

The crude $N^\alpha$-Biotin-GlY-Ser-Gln-Asn-Tyr-Pro-Ile-Val-Gly-Lys-OH was dissolved in 200 mL of a 5% acetonitrile (aqueous) solution containing 0.1% trifluoroacetic acid and then filtered through a 0.22 micron filter. The resulting solution was applied to a 2.2×25 cm. reverse phase column of octadecyl-silica (Vydac C-18) which had been equilibrated with the same buffer. The peptide was eluted using an 855 minute linear gradient of 7.5 to 25% acetonitrile, at 2 mL/minute, with collection of fractions. These fractions were analyzed using Analytical HPLC was performed on a 4.6×250 mm Vydac C-18 column using similar buffer conditions. The fractions containing the desired material were combined, frozen and lyophilized to provide 1.206 g (62%).

Amino acid analysis of the isolated $N^\alpha$-Biotin-Gly-Ser-Gln-Asn-Tyr-Pro-Ile-Val-Gly-Lys-OH gave the following ratios: Asn 1.1; Ser 0.96; Gln 1.1; Pro 1.1; Gly 2.1; Val 0.80; Ile 0.78; Tyr 1.1; Lys 1.1; in agreement with theory. Fast-atom bombardment mass spectrometry gave a molecular ion mass peak of 1288, in agreement with theory.

D. Labeling

The purified peptide was labeled with a fluorescent marker at the C-terminal end for use in the Pandex assay. $N^\alpha$-Biotin-Gly-Ser-Gln-Asn-Tyr-Pro-Ile-Val-Gly-Lys-OH (1.206 g, 0.936 mmol) was dissolved in 100 mL of 0.1M sodium borate, pH 9.5. Then, a solution of 3 g (7.7 mmol) of fluorescein isothiocyanate in 15 mL dimethylsulfoxide was added to the reaction mixture in 10 equal portions over two hours. The resulting mixture was allowed to react for one hour after the final addition. The solution was adjusted to pH 3 using 5M hydrochloric acid, resulting in the formation of a precipitate which was removed by centrifugation.

The peptide solution was then adjusted to pH 7.8 using 5N sodium hydroxide and then diluted to 200 mL total volume by the addition of 0.1M ammonium acetate, pH 7.5. The resulting solution was then filtered through a 0.22 micron filter and loaded onto a 2.2×25 cm column of Vydac C-18 which had been equilibrated with of 5% acetonitrile in 0.1M ammonium acetate (pH 7.5). The peptide was eluted from the column using an 855 minute linear gradient of 5-acetonitrile, at 2 mL/minute, with collection of fractions. Analytical HPLC was used to analyze the fractions. The fractions containing the desired product were then combined, frozen and lyophilized to provide 190.2 mg (12%).

Amino acid analysis of the purified peptide gave the following: Asn 1.1; Ser 1.0; Gln 1.1: Pro 1.1; Gly 2.1; Val 0.8; Ile 0.8; Tyr 1.1; Lys 1.0; in agreement with theory. Fast-atom bombardment mass spectrometry gave amolecular ion mass peak of 1678, in agreement with theory.

E. Fluorescence HIV-1 Protease Inhibitor Assay

The following buffers and solutions are used in the Fluorescence HIV-1 Protease Inhibitor Assay:

| | |
|---|---|
| MES-ALB Buffer: | 0.05 $\underline{M}$ 4-morpholineethane sulfonic acid, pH 5.5<br>0.02 $\underline{M}$ NaCl<br>0.002 $\underline{M}$ EDTA<br>0.001 $\underline{M}$ DTT<br>1.0 mg/mL BSA |
| TBSA Buffer: | 0.02 $\underline{M}$ TRIS<br>0.15 $\underline{M}$ NaCl<br>1.0 mg/mL BSA |
| Avidin Coated Beads Solution: | 0.1% solution of Fluoricon Avidin Assay Particles (Avidin conjugated to solid polystyrene beads, 0.6–0.8 microns in diameter in TBSA Buffer |
| Enzyme Solution: | 27 IU/mL of purified HIV-1 protease in MES-ALB buffer (1 IU equals the amount of enzyme required to hydrolyze 1 µmol of substrate per minute at 37° C. |

To each well of a round bottom, 96-well plate is added 20 µL of the Enzyme Solution followed by 10 µL of the compound to be evaluated in a 20% aqueous dimethylsulfoxide solution. Purified HIV-1 protease was obtained as described above. The resulting solution is incubated for one hour at room temperature and then 20 µL of a solution containing the substrate, $N^\alpha$-Biotin-GlY-Ser-Gln-Asn-Tyr-Pro-Ile-Val-Gly-Lys(Nε-FITC)-OH, in MES-ALB buffer (1.5 µl/mL) is added to each well. The solutions are then incubated for 16 hours at room temperature and then each well is diluted with 150 µL of MES-ALB buffer.

To each well of a second round bottom, 96-well Pandex plate is added 25 uL of the Avidin Coated Beads Solution. Then, to each well is added 25 µL of the diluted incubation solutions, prepared above. The solutions are mixed thoroughly and the plates are loaded into a Pandex® machine, washed, evacuated and read. Sample detection was performed by excitation at 485 nm, reading the resulting epifluorescence at 535 nm.

The IC$_{50}$ results obtained in the Fluorescence Assay for the compounds of the present invention are set forth below in Table 1. All values have been normalized to a positive control which is [1S-(1R*,4R*,5S*)]-N-(1-(2-amino-2-oxo-ethyl)-2-oxo-3-aza -4-phenylmethyl-5-hydroxy-6-(2-(1-t-butylamino-1-oxomethyl)phenyl)hexyl)-2-quinolinyl carboxamide.

TABLE 1

Inhibitory Activity of Formula I Compounds

| Example No. | Fluorescence Assay IC$_{50}$ in ng/mL |
|---|---|
| Control | 1.0 |
| 1A | — |
| 1B | — |
| 1C | 1.44 |
| 2 | 3.13 |
| 3 | 0.48 |
| 4 | 2.48 |
| 5A | — |
| 5B | IC$_{43}$ = 1000* |
| 5C | 0.53 |
| 6 | 2.4 |
| 7 | 0.95 |
| 8 | 2.28 |
| 9 | 1.76 |
| 10 | 1.67 |
| 11A | — |
| 11B | — |
| 11C | 7.78 |
| 12 | 1.6 |
| 13 | >10000* |
| 14 | 0.93 |
| 15 | 1.05 |
| 16 | 106 |
| 17 | IC$_{25}$ = 100* |

*the concentration of the compound was not increased above the stated concentration.

We claim:

1. A compound of formula I

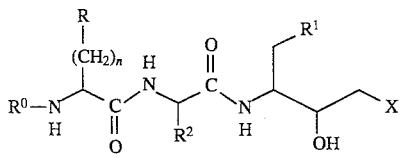

wherein:

R$^0$ is hydrogen, C$_1$–C$_6$ alkoxycarbonyl, or C$_2$–C$_6$ alkanoyl;

n is 0, 1 or 2;

R is phenyl, naphthyl or indolyl;

R$^1$ is phenyl, naphthyl or —S-R$^{1x}$, where R$^{1x}$ is phenyl or naphthyl;

R$^2$ is —CH(CH$_3$)$_2$, —CH$_2$C(O)NH$_2$, CH$_2$-imidazolyl, cyano (C$_1$–C$_4$)-alkyl, —CH$_2$SCH$_3$ or —CH$_2$C(O)-R$^{2a}$, where R$^{2a}$ is C$_1$–C$_4$ alkylamino;

X is a group having the structure:

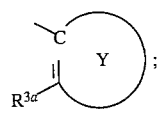

Y is phenyl or naphthyl;

R$^{3a}$ is a group having the structure:

—C(O)-NR$^4$R$^4$;

R$^4$ at each occurrence is independently hydrogen, C$_1$–C$_6$ alkyl or hydroxy (C$_1$–C$_4$) alkyl;

or a pharmaceutically acceptable salt thereof.

2. A compound according to claim 1 of the formula:

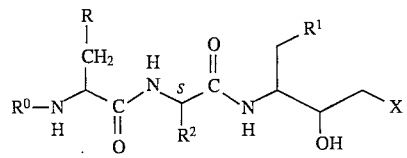

wherein:

R$^0$ is hydrogen or C$_1$–C$_4$ alkoxycarbonyl;

R$^2$ is —CH(CH$_3$)$_2$, —CH$_2$-C(O)NH$_2$ or —CH$_2$-imidazol-4-yl; and

R$^{3a}$ is —C(O)NH(t-butyl);

or a pharmaceutically acceptable salt thereof.

3. A compound according to claim 2 wherein:

R$^0$ is t-butoxycarbonyl;

R is naphth-1-yl, phenyl or indol-3-yl;

R$^2$ is —CH$_2$-C(O)NH$_2$;

R$^1$ is phenyl; and

Y is phenyl;

or a pharmaceutically acceptable salt thereof.

4. A compound according to claim 3 that is [2R- (2R*, 3S*, 6S*, 9S*)]-N-t-butyl-2- [2 -hydroxy-3-phenylmethyl-4,7-diaza -5,8-dioxo-6-(1-methylethyl)-9-N(t-butoxycarbonyl)amino-10-naphth-1-yl]decyl benzamide; or a pharmaceutically acceptable salt thereof.

5. A compound according to claim 3 that is [2R- (2R*, 3S*, 6S*, 9R*)]-N-t-butyl-2-[2-hydroxy-3-phenylmethyl-4,7-diaza -5,8-dioxo-6-(1-methylethyl)-9-N(t-butoxycarbonyl)amino-10-naphth-1-yl]decyl benzamide; or a pharmaceutically acceptable salt thereof.

6. A compound according to claim 3 that is [2R-(2R*, 3S*,6S*,9R*)]-N-t-butyl-2-[2-hydroxy-3-phenylmethyl-4,7-diaza -5,8-dioxo-6-(carbamoylmethyl)-9-N(t-butoxycarbonyl)amino-10-naphth-1-yl]decyl benzamide; or a pharmaceutically acceptable salt thereof.

7. A compound according to claim 3 that is [2R-(2R*, 3S*,6S*,9S*)]-N-t-butyl-2-[2-hydroxy-3-phenylmethyl-4,7-diaza -5,8-dioxo-6-(carbamoylmethyl)-9-N(t-butoxycarbonyl)amino-10-phenyl]decyl benzamide; or a pharmaceutically acceptable salt thereof.

8. A compound according to claim 3 that is [2R-(2R*, 3S*,6S*,9R*)]-N-t-butyl-2-[2-hydroxy-3-phenylmethyl-4,7-diaza -5,8-dioxo-6-(imidazol-4-ylmethyl)-9-N(t-butoxycarbonyl)amino-10-naphth-1-yl]decyl benzamide; or a pharmaceutically acceptable salt thereof.

9. A compound according to claim 3 that is [2R-(2R*, 3S*,6S*,9S*)]-N-t-butyl-2-[2-hydroxy-3-phenylmethyl-4,7-diaza -5,8-dioxo-6-(carbamoylmethyl)-9-N(t-butoxycarbonyl)amino-10-indol-3-yl]decyl benzamide; or a pharmaceutically acceptable salt thereof.

10. A compound according to claim 3 that is [2R-(2R*, 3S*,6S*,9R*)]-N-t-butyl-2-[2-hydroxy-3-phenylmethyl-4, 7-diaza -5,8-dioxo-6-(carbamoylmethyl)-9-N(t-butoxycarbonyl)amino-10-indol-3-yl]decyl benzamide; or a pharmaceutically acceptable salt thereof.

11. A compound according to claim 3 that is [2R-(2R*, 3S*, 6S*, 9S*)]-N-t-butyl-2-[2-hydroxy-3-phenylmethyl-4, 7-diaza -5,8-dioxo-6-(carbamoylmethyl)-9-N(t-butoxycarbonyl)amino-10-naphth-1-yl]decyl benzamide; or a pharmaceutically acceptable salt thereof.

12. A pharmaceutical formulation comprising one or more pharmaceutically acceptable carriers, diluents or excipients and a compound of claim 1.

13. A pharmaceutical formulation according to claim 12 where the compound is one of the formula:

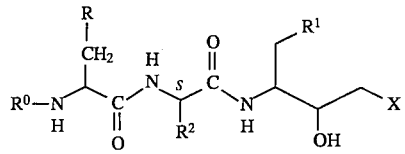

wherein:

$R^0$ is hydrogen or $C_1$–$C_4$ alkoxycarbonyl;

$R^2$ is —CH(CH$_3$)$_2$, —CH$_2$-C(O)NH$_2$ or —CH$_2$-imidazol-4-yl; and $R^{3a}$ is —C(O)NH(t-butyl);

or a pharmaceutically acceptable salt thereof.

14. A pharmaceutical formulation according to claim 13 where the compound is one wherein:

$R^0$ is t-butoxycarbonyl;

R is naphth-1-yl, phenyl or indol-3-yl;

$R^2$ is —CH$_2$-C(O)NH$_2$;

$R^1$ is phenyl; and

Y is phenyl;

or a pharmaceutically acceptable salt thereof.

15. A pharmaceutical formulation according to claim 14 where the compound is [2R-(2R*,3S*,6S*,9S*)]-N-t-butyl-2-[2-hydroxy-3 -phenylmethyl-4,7-diaza-5,8-dioxo-6-(1-methylethyl)-9-N(t-butoxycarbonyl)amino-10-naphth-1 yl]decyl benzamide; or a pharmaceutically acceptable salt thereof.

16. A pharmaceutical formulation according to claim 14 where the compound is [2R-(2R*,3S*, 6S*, 9R*)]-N-t-butyl-2-[2-hydroxy-3 -phenylmethyl-4,7-diaza-5,8-dioxo-6-(1-methylethyl)-9-N(t-butoxycarbonyl)amino-10-naphth-1yl]decyl benzamide; or a pharmaceutically acceptable salt thereof.

17. A pharmaceutical formulation according to claim 14 where the compound is [2R-(2R*,3S*, 6S*, 9R*)]-N-t-butyl-2-[2-hydroxy-3 -phenylmethyl-4,7-diaza-5,8-dioxo-6-(carbamoylmethyl)-9-N(t-butoxycarbonyl)amino-10-naphth-1yl]decyl benzamide; or a pharmaceutically acceptable salt thereof.

18. A pharmaceutical formulation according to claim 14 where the compound is [2R-(2R*,3S*,6S*,9S*)]-N-t-butyl-2-[2-hydroxy-3 -phenylmethyl-4,7-diaza-5,8-dioxo-6-(carbamoylmethyl)-9-N(t-butoxycarbonyl)amino-10phenyl]decyl benzamide; or a pharmaceutically acceptable salt thereof.

19. A pharmaceutical formulation according to claim 14 where the compound is [2R-(2R*,3S*,6S*, 9R*)]-N-t-butyl-2-[2-hydroxy-3 -phenylmethyl-4,7-diaza-5,8-dioxo-6-(imidazol-4-ylmethyl)-9-N(t-butoxycarbonyl)amino-10-naphth1-yl] decyl benzamide; or a pharmaceutically acceptable salt thereof.

20. A pharmaceutical formulation according to claim 14 where the compound is [2R-(2R*,3S*,6S*,9S*)]-N-t-butyl-2-[2-hydroxy-3 -phenylmethyl-4,7-diaza-5,8-dioxo-6-(carbamoylmethyl)-9-N(t-butoxycarbonyl)amino-10-indol-3yl] decyl benzamide; or a pharmaceutically acceptable salt thereof.

21. A pharmaceutical formulation according to claim 14 where the compound is [2R-(2R*, 3S*, 6S*, 9R*)]-N-t-butyl-2-[2-hydroxy-3 -phenylmethyl-4,7-diaza-5,8-dioxo-6-(carbamoylmethyl)-9-N(t-butoxycarbonyl)amino-10-indol-3-yl]decyl benzamide; or a pharmaceutically acceptable salt thereof.

22. A method of inhibiting HIV replication comprising administering to an HIV infected cell, a cell susceptible to HIV infection or a primate in need thereof an effective amount of a compound of claim 1.

23. A method according to claim 22 where the compound is one of the formula:

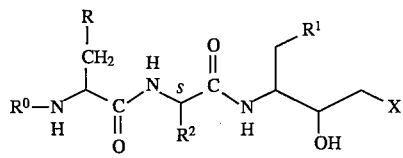

wherein:

$R^0$ is hydrogen or $C_1$–$C_4$ alkoxycarbonyl;

$R^2$ is —CH(CH$_3$)$_2$, —CH$_2$-C(O)NH$_2$ or —CH$_2$-imidazol-4-yl; and $R^{3a}$ is —C(O)NH(t-butyl);

or a pharmaceutically acceptable salt thereof.

24. A method according to claim 23 where the compound is one wherein:

$R^0$ is t-butoxycarbonyl;

R is naphth-1-yl, phenyl or indol-3-yl;

$R^2$ is —CH$_2$-C(O)NH$_2$;

$R^1$ is phenyl; and

Y is phenyl;

or a pharmaceutically acceptable salt thereof.

25. A method according to claim 24 where the compound is [2R- (2R*, 3S*, 6S*, 9S*)]-N-t-butyl-2-[2 -hydroxy-3-phenylmethyl-4,7 -diaza-5,8-dioxo-6-(1-methylethyl)-9-N(t-butoxycarbonyl)amino-10-naphth-1-yl]decyl benzamide; or a pharmaceutically acceptable salt thereof.

26. A method according to claim 24 where the compound is [2R-(2R*, 3S*, 6S*, 9R*)]-N-t-butyl-2-[2-hydroxy-3-phenylmethyl-4,7 -diaza-5,8-dioxo-6-(1-methylethyl)-9-N(t-butoxycarbonyl)amino-10-naphth-1-yl]decyl benzamide; or a pharmaceutically acceptable salt thereof.

27. A method according to claim 24 where the compound is [2R-(2R*,3S*,6S*,9R*)]-N-t-butyl-2-[2-hydroxy-3-phenylmethyl-4,7-diaza -5,8-dioxo-6-(carbamoylmethyl)-9-N(t-butoxycarbonyl)amino-10-naphth-1-yl]decyl benzamide; or a pharmaceutically acceptable salt thereof.

28. A method according to claim 24 where the compound is [2R-(2R*, 3S*, 6S*, 9S*)]-N-t-butyl-2-[2-hydroxy-3-phenylmethyl-4,7 -diaza-5,8-dioxo-6-(carbamoylmethyl)-9-3-phenylmethyl-4,7 -N(t-butoxycarbonyl)amino-10-phenyl] decyl benzamide; or a pharmaceutically acceptable salt thereof.

29. A method according to claim 24 where the compound is [2R-(2R*, 3S*, 6S*, 9R*)]-N-t-butyl-2-[2-hydroxy-3-phenylmethyl-4,7 -diaza-5,8-dioxo-6-(imidazol-1-ylmethyl)-9-N(t-butoxycarbonyl)amino-10-naphth-1-yl]decyl benzamide; or a pharmaceutically acceptable salt thereof.

30. A method according to claim 24 where the compound is [2R-(2R*, 3S*, 6S*, 9S*)]-N-t-butyl-2-[2-hydroxy-3- phenylmethyl-4,7 -diaza-5,8-dioxo-6-(carbamoylmethyl)-9-N(t-butoxycarbonyl)amino-10-indol-3-yl]decyl benzamide; or a pharmaceutically acceptable salt thereof.

31. A method according to claim 24 where the compound is [2R-(2R*,3S*,6S*,9R*)]-N-t-butyl-2-[2-hydroxy-3-phenylmethyl-4,7 -diaza-5,8-dioxo-6-(carbamoylmethyl)-9-N(t-butoxycarbonyl)amino-10-indol-3-yl]decyl benzamide; or a pharmaceutically acceptable salt thereof.

32. A method according to claim 24 where the compound is [2R-(2R*,3S*,6S*,9S*)]-N-t-butyl-2-[2-hydroxy-3-phenylmethyl-4,7 -diaza-5,8-dioxo-6-(carbamoylmethyl)-9-N(t-butoxycarbonyl)amino-10-naphth-1-yl]decyl benzamide; or a pharmaceutically acceptable salt thereof.

* * * * *